(12) United States Patent
Hu

(10) Patent No.: US 10,196,701 B2
(45) Date of Patent: Feb. 5, 2019

(54) HEPATITIS B VIRUS CAPSID ASSEMBLY

(71) Applicant: The Penn State Research Foundation, University Park, FL (US)

(72) Inventor: Jianming Hu, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/155,503

(22) Filed: May 16, 2016

(65) Prior Publication Data

US 2016/0348188 A1   Dec. 1, 2016

Related U.S. Application Data

(60) Provisional application No. 62/169,236, filed on Jun. 1, 2015.

(51) Int. Cl.

| C12Q 1/70 | (2006.01) |
|---|---|
| C07K 14/005 | (2006.01) |
| C12N 7/00 | (2006.01) |
| G01N 33/569 | (2006.01) |
| G01N 33/576 | (2006.01) |

(52) U.S. Cl.
CPC ............ *C12Q 1/706* (2013.01); *C07K 14/005* (2013.01); *C12N 7/00* (2013.01); *G01N 33/56983* (2013.01); *G01N 33/5762* (2013.01); *C12N 2730/10122* (2013.01); *G01N 2333/005* (2013.01); *G01N 2500/20* (2013.01)

(58) Field of Classification Search
None
See application file for complete search history.

(56) References Cited

U.S. PATENT DOCUMENTS

| 5,288,514 | A | 2/1994 | Ellman |
|---|---|---|---|
| 5,432,272 | A | 7/1995 | Benner |
| 5,474,796 | A | 12/1995 | Brennan |
| 5,506,337 | A | 4/1996 | Summerton et al. |
| 5,519,134 | A | 5/1996 | Acevedo et al. |
| 5,525,735 | A | 6/1996 | Gallop et al. |
| 5,539,083 | A | 7/1996 | Cook et al. |
| 5,549,974 | A | 8/1996 | Holmes |
| 5,569,588 | A | 10/1996 | Asby et al. |
| 5,593,853 | A | 1/1997 | Chen et al. |
| 5,605,662 | A | 2/1997 | Heller et al. |

FOREIGN PATENT DOCUMENTS

| WO | WO9119735 | 12/1991 |
|---|---|---|
| WO | WO9200091 | 1/1992 |
| WO | WO9320242 | 10/1993 |
| WO | WO95251116 | 9/1995 |
| WO | WO9535505 | 12/1995 |

OTHER PUBLICATIONS

Trepo, C. et al, "Hepatitis B virus infection", Lancet, vol. 384, No. 9959, pp. 2053-2063, DOI: http://dx.doi.org/10.1016/S0140-6736(14)60220-8, (2014) (Abstract).
Summers, J. et al, "Replication of the genome of a hepatitis B-like virus by reverse transcription of an RNA Intermediate", Cell, vol. 29, pp. 403-415, (1982) (Abstract).
Seeger, C. et al "Hepadnavirus", Fields Virology, Philadelphia, PA, Lippincott, Williams & Wilkins, Chapter 68, pp. 2185-2221, (2013).
Steven, A. et al, "Structure, assembly, and antigenicity of hepatitis B virus capsid proteins", Adv Virus Res, vol. 64, pp. 125-164, (Feb. 2005).
Zhou, S. et al, "Hepatits B virus capsid particles are assembled from core-protein dimer precursors", Proc Natl Acad Sci USA, vol. 89, pp. 10046-10050, (1992).
Wynne S. et al, "The crystal structure of the human hepatitis B virus capsid", Mol Cell, vol. 3, pp. 771-780, (1999).
Wingfield, P. et al, "Hepatitis core antigen produced *escherichia coli*: Subunit composition, conformational analysis, and in vitro capsid assembly", Biochemistry, vol. 34, pp. 4919-4932, (1995) (Abstract).
Lanford, R. et al, "Expression and characterization of hepatitis B virus precore-core antigen in *E. coli*", Virology, vol. 176, pp. 222-233, (1990) (Abstract).
Birnbaum, F. et al, "Hepatitis B virus nucleocapsid assembly: primary structure requirements in the core protein", J Virol, vol. 64, pp. 3319-3330, (1990).
Gallina, A. et al, "A recombinant hepatitis B core antigen polypeptide with the protamine-like domain deleted self-assemblies into capsid particles but fails to bind nucleic acids", J Virol, vol. 63, pp. 4645-4652, (1989).
Hatton T. et al, "RNA- and DNA-binding activities in hepatitis B virus capsid protein: a model for their roles in viral replication", J Virol, vol. 66(9), pp. 5232-5241, (Sep. 1992).
Chu, T. et al, "Nucleic acid chaperone activity associated with the Arginine-rich domain of hepatitis B virus core protein", J Virol, vol. 88, pp. 2530-2543, (2014).
Nassal, M. "The Arginine-rich domain of the hepatitis B virus core protein is required for pregenome encapsidation and productive viral positive-strand DNA synthesis but not for virus assembly", J. Virol, vol. 66, pp. 4107-4116, (1992).
Yu, M. et al, "Multiple functions of capsid protein phosphorylation in duck hepatitis B virus replication", J Virol, vol. 68, pp. 4341-4348, (1994).
Liao, W. et al, "Phosphorylation and nuclear localization of the hepatitis B virus core protein: significance of serine in the three repeated SPRRR motifs", J Virol, vol. 69, pp. 1025-1029, (1995).
Machida, A. et al, "Phosphorylation in the carboxyl-terminal domain for the capsid protein of Hepatitis B virus: evaluation with a monoclonal antibody", J Virol, vol. 65, pp. 6024-6030, (1991).

(Continued)

*Primary Examiner* — Stacy B Chen

(74) *Attorney, Agent, or Firm* — McHale & Slavin, P.A.

(57) ABSTRACT

Cell-free translation and assembly systems allow for HBV capsid assembly under cell-free conditions that also mimic the physiological salt and protein concentrations. These hepatitis virus capsid assembly systems utilize the C-terminal domain (CTD) and N-terminal domain (NTD) of the hepatitis capsid protein in capsid assembly. Uses of the system include the identification of potential new therapeutic strategies and screening of potential therapeutic agents which target these domains and modulate capsid assembly and/or disassembly and other functions of these domains in HBV replication and pathogenesis.

4 Claims, 10 Drawing Sheets

Specification includes a Sequence Listing.

(56) References Cited

OTHER PUBLICATIONS

Kann, M. et al, "Effect of core protein phosphorylation by protein kinase C on encapsidation of RNA within core particles of Hepatitis B virus", J Virol, vol. 68, pp. 7993-8000, (1994).
Basagoudanavar, S. et al, "Regulation of hepadnavirus reverse transcription by dynamic nucleocapsid phosphorlylation", J Virol, vol. 81, pp. 1641-1649, (2007).
Perlman, D. et al, "Reverse transcription-associated dephosphorylation of hepadnavirus nucleocapsids", Proc Natl Acad Sci USA, vol. 102, pp. 9020-9025, (2005).
Gazina, E. et al, "Core protein phosphorylation modulaters pregenomic RNA encapsidation to different extents in human and duck hepatitis B viruses", J Virol, vol. 74, pp. 4721-4728, (2000).
Lan Y. et al, "Roles of the three major phosphorylation sites of hepatitis B virus core protein in viral replication", Virology, vol. 259, pp. 342-348, (1999).
Lewellyn, E. et al, "Serine phosphoacceptor sites within the core protein of hepatitis B virus contribute to genome replication pleiotropically: e17202", PLoS One 6, p. e17202, (2011).
Liu, K. et al, "Regulation of multiple stages of hepadnavirus replication by the carboxyl-terminal domain of viral core protein in trans", J Virol, vol. 89, pp. 2918-2930, (2015).
Porterfield, J. et al, "Full-length hepatitis B virus core protein packages viral and heterologous RNA with similarly high levels of cooperativity", J. Virol, vol. 84, pp. 7174-7184, (2010).
Jung, J. et al, "Phosphoacceptors threonine 162 and serines 170 and 178 within the carboxyl-terminal RRRS/T motif of the hepatitis B virus core protein make multiple contributions to hepatitis B virus replication", J Virol, vol. 88, pp. 8754-8767, (2014).
Hilditch, C. et al, "Physiochemical analysis of the hepatitis B virus core antigen produced by a baculovirus expression vector", J Gen Virol, Pt 11, pp. 2755-2759, (1990).
Ning, X. et al, "Secretion of genome-free hepatitis B virus—single strand blocking model for Virion morphogenesis of pararetrovirus", PLoS Pathogens 7, p. e1002255, (2011).
Ludgate, L. et al, "Cell-free hepatitis B virus capsid assembly dependent on the core protein C-terminal domain and regulated by phosphorylation", PLoS One 6, p. e29566, (2011).
Ludgate, L. et al, "Cyclin-dependent kinase 2 phosphorylates S/T-P sites in the hepadnavirus core protein C-terminal domain and is incorporated into viral capsids", J Virol, vol. 86, pp. 12237-12250, (2012).
Le Pogam, S. et al, "Exposure of RNA templates and encapsidation of spliced viral RNA are influenced by the arginine-rich domain of human hepatitis B virus core antigen (HBcAg 165-173)", J Virol, vol. 79, pp. 1871-1887, (2005).
Chua, P. et al, "Testing the balanced electrostatic interaction hypothesis of hepatitis B virus DNA synthesis by using an In Vivo charge rebalance approach", J Virol, vol. 84, pp. 2340-2351, (2010).
Nguyen, D. et al, "Reverse transcriptase- and RNA packaging signal-dependent incorporation of APOBEC3G into hepatitis B virus nucleocapsids", J Virol, vol. 82, pp. 6852-6861, (2008).
Freier, S. et al, "The ups and downs of nucleic acid duplex stability: structure-stability studies on chemically-modified DNA:RNA duplexes", Nucl Acid Res, 25:22:4429-4443, (1997).
Toulme, J., "New candidates for true antisense", Nature Biotechnology, vol. 19, pp. 17-18, (2001).
Manoharan, M., "2'-carbohydrate modifications in antisense oligonucleotide therapy: importance of conformation, configuration and conjugation", Biochemica et Biophysica Acta—Gene structure and expression, vol. 1489, pp. 117-139, (1999) (Abstract).
Uhlman, E., "Recent advances in the medicinal chemistry of antisense oligonucleotides", Drug Discovery & Development, vol. 3, pp. 203-213, (2000) (Abstract).
Herdewijn, P., "Antisense and nucleic acid drug development", Antisense & Nucleic Acid Drug Dev, vol. 10, pp. 297-310, (2000) (Abstract).
Christensen, K. et al, "A novel class of oligonucleotide analogues containing 2-40 -O,3'-C-linked [3.2.0] bicycloarabinonucleoside monomers: synthesis, thermal affinity studies, and molecular modeling", J Am Chem Soc, vol. 120, pp. 5458-5463, (1998) (Abstract).
Prakash, T. et al, "2-40 -modified oligonucleotides for antisense therapeutics", Cur Top Med Chem, 7(7):641-649, (2007) (Abstract).
Cho, E. et al, "Applications of aptamers as sensors", Annual Review of Analytical Chemistry, vol. 2, pp. 241-264, (2009) (Abstract).
Kornberg, A., "xxxxx", W.H. Freeman, San Francisco, CA, pp. 75-77, (1980).
Gebeyehu, G. et al, "Novel biotinylated nucleotide—analogs for labeling and colorimetric detection of DNA", Nucl Acids Res, vol. 15, p. 4513, (1987).
Sanghvi, Y., "xxxxx", Antisense Research and Applications, CRC Press, Boca Raton, FL, pp. 276-278, (1993).
Letsinger, R. et al, "Cholesterol-conjugated oligonucleotides: synthesis, properties, and activity as inhibitors of replication of human immunodeficiency virus in cell culture", Proc Natl Acad Sci USA, vol. 86, p. 6553, (1989).
Manoharan, M. et al, "Cholic acid-oligonucleotide conjugates for antisense applications", Bioorg Med Chem Let, vol. 4, p. 1053, (1994) (Abstract).
Manoharan, M. et al, "Chemical modifications to improve uptake and bioavailability of antisense oligonucleotides", Ann N.Y. Acad Sci, vol. 660, p. 306, (1992) (Abstract).
Manoharan, M. et al, "Introduction of a lipophilic thioether tether in the minor groove of nucleic acids for antisense applications", Bioorg Med Chem Let, vol. 3, p. 2765, (1993) (Abstract).
Oberhauser, B. et al, "Effective incorporation of 2'-O-methyloligonucleotides into liposomes and enhanced cell association through modification with thiocholesterol", Nucl Acids Res, vol. 20, p. 533, (1992).
Saison-Behmoaras, T. et al, "Short modified antisense oligonucleotides directed against Ha-ras point mutation induce selective cleavage of the mRNA and inhibit T24 cells proliferation", EMBO J, vol. 10, p. 111, (1991).
Kabanov A. et al, "A new class of antivirals: antisense oligonucleotides combined with a hydrophobic substituent effectively inhibit influenza virus reproduction and synthesis of virus-specific proteins in MDCK cells", FEBS Lett, vol. 259, p. 327, (1990) (Abstract).
Svinarchuk, F. et al, "Inhibition of HIV proliferation of MT-4 cells by antisense oligonucleotide conjugated to lipophilic groups", Biochimie, vol. 75(1-2), p. 49-54, (1993) (Abstract).
Manoharan, M. et al, "Lipidic nucleic acids", Tetrahedron Lett, vol. 36, p. 3651-3654, (1995) (Abstract).
Shea, R. et al, "Synthesis, hybridization properties and antiviral activity of lipid-oligodeoxynucleotide conjugates", Nucl Acids Res, vol. 18, p. 3777-3783, (1990).
Manoharan, M. et al, "Oligonucleotide conjugates: alteration of the pharmacokinetic properties of antisense agents", Nucleosides & Nucleotides, vol. 14, p. 969-973, (1995) (Abstract).
Czarnik, A. "Encoding methods for combinatorial chemistry", Curr Opin Chem Bio, vol. 1, p. 60-66, (1997) (Abstract).
Thompson, L. et al, "Synthesis and applications of small molecule libraries", Chem Rev, vol. 96, pp. 555-600, (1996).
Kenan, D. et al, "Exploring molecule diversity with combinatorial shape libraries", Trends Biochem Sci, vol. 19, pp. 57-64, (1994) (Abstract).
Janda, K., "Tagged verses untagged libraries: methods for the generation and screening of combinatorial chemical libraries", Natl Acad Sci USA, vol. 91, pp. 10779-10785, (1994).
Lebl, xx. et al, "One-bead-one-structure combinatorial libraries", Biopolymers, vol. 37, pp. 177-198, (1995) (Abstract).
Eichler, xx, et al, "Peptide, peptidomimetic, and organic synthetic combinatorial libraries", Med Res Rev, vol. 15, pp. 481-496, (1995) (Abstract).
Chabala, J., "Solid-phase combinatorial chemistry and novel tagging methods for identifying leads", Curr Opin Biotechnol, vol. 6, pp. 632-639, (1995) (Abstract).
Dolle, R., "Discovery of enzyme inhibitors through combinatorial chemistry", Mol Divers, vol. 2, pp. 223-236, (1997) (Abstract).
Fauchere, J. et al, "Peptide and nonpeptide lead discovery using robotically synthesized soluble libraries", Can J Physiol Pharmacol, vol. 75, pp. 683-689, (1997) (Abstract).

(56) References Cited

OTHER PUBLICATIONS

Eichler, J. et al, "Generation and utilization of synthetic combinatorial libraries", Mol Med Today, vol. 1, pp. 174-180, (1995) (Abstract).

Kay, B. et al, "Identification of enzyme inhibitors from phage-displayed conbinatorial peptide libraries", Comb Chem High Throughput Screen, vol. 4, p. 535-543, (2001).

DeWitt, S. et al, ""Diversomers": an approach to nonpeptide, nonoligomeric chemical diversity", Proc Natl Arad Sci USA, vol. 90, pp. 6909-6913, (1993).

Hagihara, M. et al, "Vinylogous polypeptides", J Amer Chem Soc, vol. 114, p. 6568-6570, (1992) (Abstract).

Hirschmann, R. et al, "Nonpeptidal peptidomimetics with .beta-D-glucose scaffolding. A partial somatostatin agonist bearing a close structural relationship to a potent, selective substance P antagonist", J Amer Chem Soc, vol. 114, pp. 9217-9218, (1992) (Abstract).

Chen, C. et al, "Analogous" organic synthesis of small-compound libraries: validation of combinatorial chemistry in small-molecule synthesis, J. Amer Chem Soc, vol. 116, pp. 2661, (1994) (Abstract).

Cho, C. et el, "An unnatural biopolymer", Science, vol. 261, p. 1303-1305, (1993) (Abstract).

Campbell, D. et al, "Phosphonate ester synthesis using a modified mitsunobu condensation", J. Org. Chem., vol. 59, pp. 658-660, (1994) Abstract.

Vaughan, T. et al, "Human antibodies with sub-nanomolar affinities isolated from a large non-immunized phage display library", Nature Biotechnology, 14(3):309-314, (1996) (Abstract).

Liang, R. et al, "Parallel synthesis and screening of a solid phase carbohydrate library", vol. 274, pp. 1520-1522, (1996) (Abstract).

Baum, R, "Solid-phase synthesis of benzodiazepines", C&E News, p. 33-34, (Jan. 18, 1993) (Abstract).

Deres, K. et al, "Inhibition of hepatitis B virus replication by drug-induced depletion of nucleocapsids", Science, 299 (5608), pp. 893-896, (Feb. 2003) Abstract.

Schena, M. et al, "Parallel human gene analysis: microarray-based expression monitoring of 1000 genes", Proc Natl Acad Sci USA, vol. 93, pp. 10614-10619, (1996).

Heller, R. et al, "Discovery and analysis of inflammatory disease-related genes using cDNA microarrays", Proc Natl Acad Sci USA, vol. 94, pp. 2150-2155, (1997).

Merrifield, R., "Solid phase peptide synthesis. II. The synthesis of Bradykinin", J Amer Chem Soc, vol. 85, pp. 2149-2154, (1963) (Abstract).

Geysen, H. et al, "Strategies for epitope analysis using peptides synthesis", J Immun Meth, vol. 102, pp. 259-274, (1987) (Abstract).

Frank, R. et al, "Simultaneous multiple peptide synthesis under continuous flow conditions on cellulose paper discs as segmental solid supports", Tetrahedron, vol. 44, pp. 6031-6040, (1988) (Abstract).

Fodor, S. et al, "Light-directed, spatially addressable parallel chemical synthesis", Science, vol. 251, pp. 767-777, (1991).

Sheldon, E. et al, "Matrix DNA hybridization", Clinical Chemistry, 39(4):718-719, (1993).

Kozal, M. et al, "Extensive polymorphisms observed in HIV-1 clade B protease gene using high-density oligonucleotide arrays", Nature Medicine, 2(7):753-759, (1996) (Abstract).

Hu, J. et al, "Hsp90 is required for the activity of a hepatitis B virus reverse transcriptase", Proc Natl Acad Sci USA, vol. 93, 1060-1064, (1996).

Cohen, P. et al, "Okadaic acid: a new probe for the study of cellular regulation", Trends Biochem Sci, vol. 15, pp. 98-102, (1990) (Abstract).

Seifer, M. et al, "A micromolar pool of antigenetically distinct precursors is required to initiate cooperative assembly of hepatitis B virus capsids in Xenopus Oocytes", J Virol, vol. 67, pp. 249-257, (1993).

Tan, Z. et al, "Genetically altering the thermodynamics and kinetics of hepatitis B virus capsid assembly has profound effects on virus replication in cell culture", Journal of Virol, vol. 87, pp. 3208-3216, (2013).

Lingappa, J. et al, "A eukaryotic cytosolic chaperonin is associated with a high molecular weight intermediate in the assembly of hepatitis B virus capsid, a multimeric particle", J. Cell Biol., vol. 125, No. 1, pp. 99-111, (Apr. 1994).

Stray, S. et al, "A heteroaryldihydropyrimidine activates and can misdirect B virus capsid assembly", PNAS, vol. 102, No. 23, pp. 8138-8143, (Jun. 2005).

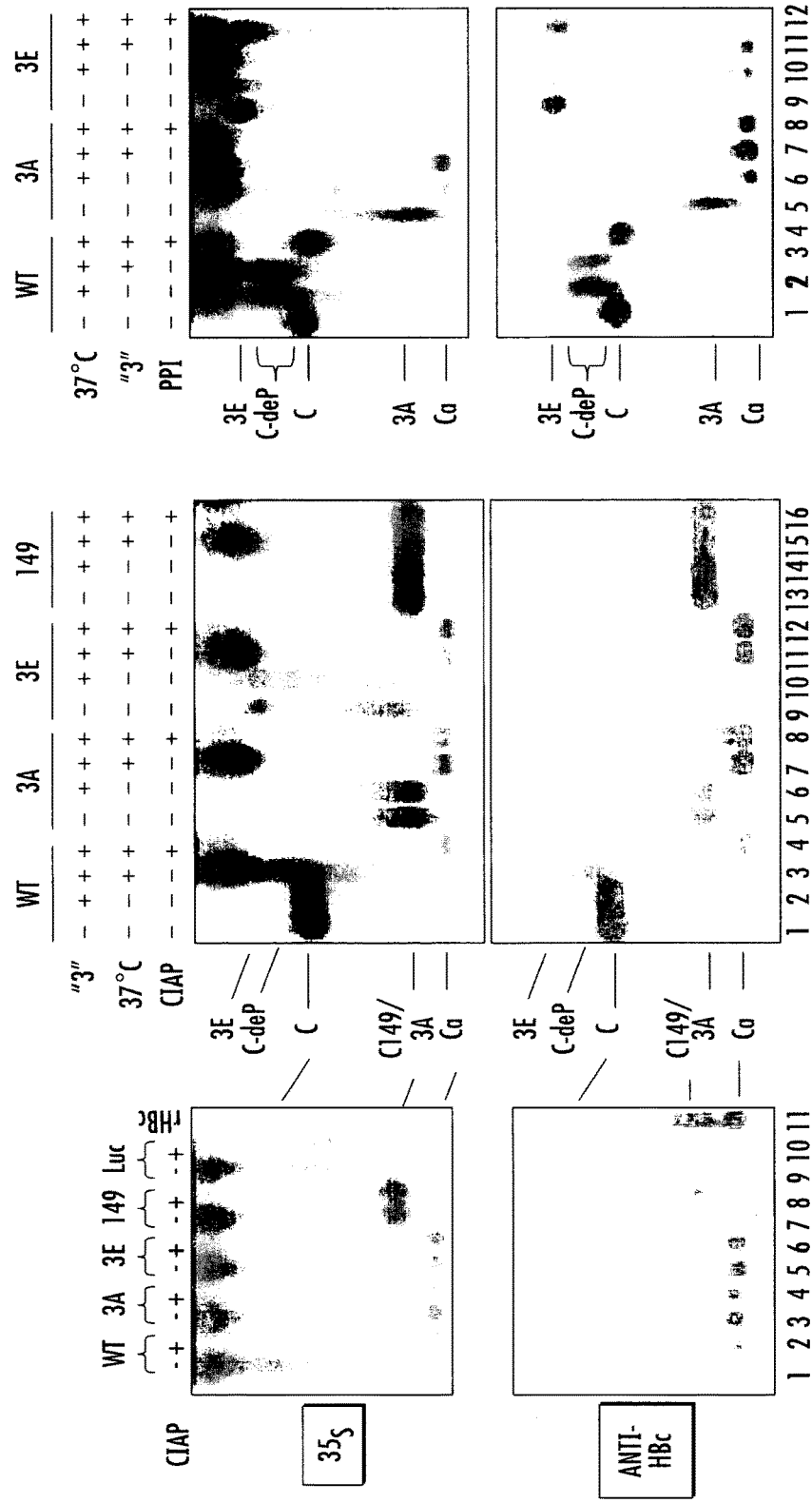

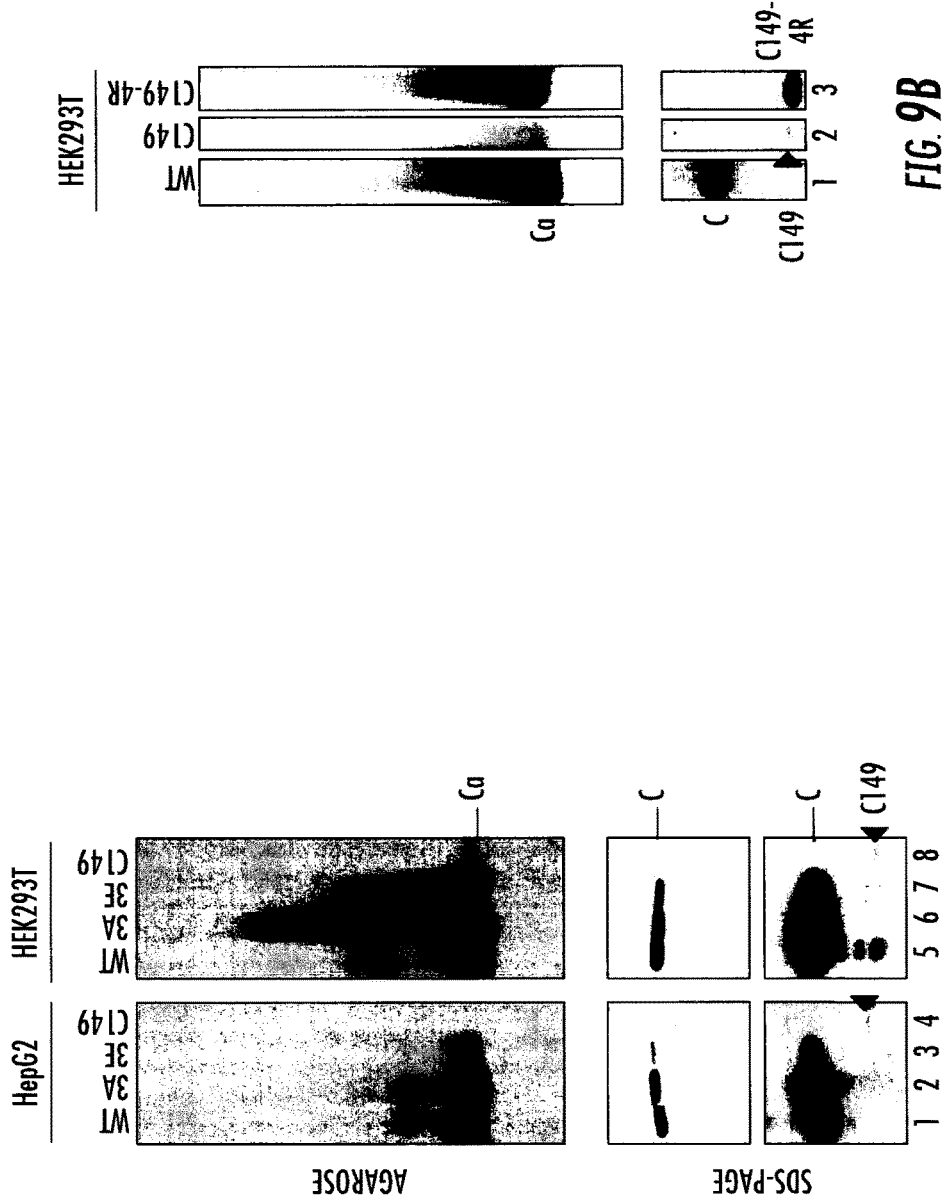

HEPATITIS B VIRUS CAPSID ASSEMBLY

CROSS REFERENCE TO RELATED APPLICATIONS

In accordance with 37 C.F.R. § 1.76, a claim of priority is included in an Application Data Sheet filed concurrently herewith. The present application is a U.S. patent application which claims priority to U.S. Provisional Patent Application No. 62/169,236 filed Jun. 1, 2015, the complete disclosure of which is herein incorporated by reference.

STATEMENT REGARDING FEDERALLY SPONSORED RESEARCH

This invention was made with government support under Grant No. AI043453, awarded by the National Institutes of Health. The Government has certain rights in the invention.

FIELD OF THE INVENTION

Embodiments of the invention are directed to hepatitis virus capsid assembly in cell-free systems. Therapeutic agents are identified by their ability to inhibit the assembly of the capsid and other functions attributed to the capsid protein.

BACKGROUND

Hepatitis B virus (HBV) remains an important global pathogen that chronically infects hundreds of millions of people worldwide and causes hepatitis, cirrhosis and liver cancer (Trepo C., et al. (2014). *Lancet*, 384(9959):2053-2063). HBV is an enveloped virus with an inner capsid shell, which in turn encloses a small (3.2 kbp) DNA genome. As a member of the Hepadnaviridae family, which also includes related animal viruses like the duck hepatitis B virus (DHBV), HBV replicates its DNA genome via reverse transcription of a RNA intermediate called pregenomic RNA (pgRNA) (Summers J, Mason W S (1982). *Cell* 29: 403-415; Seeger C, et al. (2013) Hepadnaviruses. In: Knipe D M, Howley P M, editors. Fields Virology. Philadelphia: Lippincott, Williams & Wilkins. pp. 2185-2221). HBV assembly begins with the assembly of a nucleocapsid (NC) that packages specifically a copy of pgRNA, in complex with the virally-encoded reverse transcriptase (RT) protein (Hu J, Seeger C (2015) Hepadnavirus Genome Replication and Persistence. In: Seeger C, Locarnini S, editors. Cold Spring Harb Perspect Med: Cold Spring Harbor Laboratory Press). The pgRNA is then converted to DNA within the NC by the RT protein.

The icosahedral HBV capsid shell enclosing the viral RNA or DNA is composed of multiple copies of a single viral protein, the HBV core or capsids protein (C or HBc). This small (ca. 21 kd) protein has multiple essential functions in the viral life cycle: including assembly into capsids, packaging of the viral pgRNA and RT protein, regulation of viral reverse transcription, NC envelopment and virion secretion, and nuclear import of the viral genome (Seeger, C. et al., Id. Hu, J. et al., Id). HBc can be divided into a N-terminal domain (NTD, from position 1-140), responsible for capsid assembly (thus also called assembly domain) and a C-terminal domain (CTD, 149-183 or 185 depending on the strains), which are connected by a linker region (140-149) (Steven A C, et al. (2005). *Adv Virus Res* 64: 125-164). The basic building blocks of the HBV capsids are HBc dimers, with 90 or 120 dimers self-assembling into T=3 or T=4 icosahedral capsid (Zhou S, et al. (1992). *Proc Natl Acad Sci USA* 89: 10046-10050; Wynne S A, et al., (1999). *Mol Cell* 3: 771-780; Wingfield P T, et al., (1995). *Biochemistry* 34: 4919-4932). In heterologous overexpression systems including bacteria and insect cells and in vitro assembly reactions using purified protein, NTD alone, without CTD, is clearly sufficient for assembly into capsids morphological similar to authentic capsids assembled from full-length HBc (Wingfield P T, et al., (1995). *Biochemistry* 34: 4919-4932; Lanford R E, et al., (1990). *Virology* 176: 222-233; Birnbaum F, Nassal M (1990). *J Virol* 64: 3319-3330; Gallina A, et al. (1989). *J. Virol* 63: 4645-4652). On the other hand, the arginine-rich (protamine-like) and highly basic CTD displays non-specific RNA and DNA binding and nucleic acid chaperone activities (Hatton T, et al., (1992). *J Virol* 66: 5232-5241; Chu T H, et al., (2014). *J Virol* 88: 2530-2543), plays essential roles in viral RNA packaging and DNA synthesis, and regulates nuclear localization of HBc (Nassal M (1992). *J Virol* 66: 4107-4116; Yu M, Summers J (1994). *J Virol* 68: 4341-4348; Liao W, Ou J H (1995). *J Virol* 69:1025-1029.

SUMMARY

This Summary is provided to present a summary of the invention to briefly indicate the nature and substance of the invention. It is submitted with the understanding that it will not be used to interpret or limit the scope or meaning of the claims.

Embodiments of the invention are directed, inter alia, to methods of identifying agents for inhibiting Hepatitis virus e.g. HBV capsid assembly and/or promote or induce capsid disassembly. In one embodiment, the method comprises contacting a composition having one or more hepatitis virus C-terminal Domain (CTD) and N-terminal Domain (NTD) nucleic acids, polynucleotides, oligonucleotides proteins, peptides, mutants or fragments thereof, with one or more candidate therapeutic compounds. In preferred embodiments the composition is a cell-free composition. The cell free system can comprise various components, such as, for example, one or more transcription factors, translation factors, nucleic acids, oligonucleotides, polynucleotides, RNA oligonucleotides, RNA polynucleotides, DNA oligonucleotides, DNA polynucleotides peptides, polypeptides, proteins, chaperones, detectable labels, or combinations thereof. The method identifies candidate therapeutic agents that would be of importance in preventing or treating hepatitis virus (e.g. HBV) infections, by, for example, inhibits assembly of the capsid. In other embodiments, a candidate therapeutic agent modulates expression, function, activity of various molecules, such as for example, RNA binding activity, DNA-binding activity, protein binding activity and/or modulates the phosphorylation/dephosphorylation of CTD and/or NTD molecules. In preferred embodiments, the method is a high-throughput screening (HTS) assay.

In certain embodiments, a Hepatitis B virus capsid (HBc) molecule comprises an N-terminal domain (NTD) molecule, a C-terminal domain (CTD) molecule, fragments, mutants, variants or combinations thereof. In some embodiments, the HBc further comprises a linker molecule linking the NTD and CTD molecules. In some embodiments, the NTD or CTD molecules are optionally truncated at an N-terminal end or C-terminal end or at both N-terminal and C-terminal ends. In some embodiments, wherein the NTD and CTD molecules are oligonucleotides or polynucleotides. In certain embodiments, the CTD molecules further comprise one or more nucleobase mutations, substitutions, insertions, deletions, variants, analogs, or combinations thereof. The one or more nucleobase mutations, substitutions, insertions, deletions, analogs or variants thereof, can in some embodiments occur at one or more CTD phosphorylation sites comprising S155, S162, S170, T160, S168, S176 or S178. In another embodiment, the Hepatitis B virus capsid molecules are peptides or polypeptides. Amino acid sequences encoding NTD and/or CTD peptides or polypeptides further comprise one or more mutants, deletions, insertions, substitutions, variants or combinations thereof.

Other aspects are described infra.

BRIEF DESCRIPTION OF THE DRAWINGS

FIG. 1A is a schematic diagram of HBc domain structure and the CTD sequence (SEQ ID NO: 1). The three major phosphorylation sites in CTD (S155, S162, and S170) are marked above the sequence and the 4 minor sites (T160, S168, S176, and S178) below. 3A and 3E have the three major sites changed to A or E respectively, whereas 7A and 7E have all seven sites substituted. FIG. 1B is a scan of a blot showing the estimation of HBc concentration as expressed in RRL. Each lane contained 3 µL RRL translation $^{35}$S signals detected by autoradiography (top). Core proteins were also detected by the mAb against the core N-terminal sequence (bottom). C, full-length HBc protein; C149, C-terminally truncated HBc protein (terminated at position 149).

FIGS. 2A-2C show HBV capsid assembly in RRL and effects of exogenous phosphatase and phosphatase inhibitors on assembly. Each lane contained 3 µL translation reaction. rHBC (purified from E. coli) loaded was 3.125 ng (A, lane 11). $^{35}$S signals detected by autoradiography (top). Core proteins were also detected by the mAb against the core N-terminal sequence (bottom). Ca, native capsids; C149, C-terminally truncated HBc protein (terminated at position 149); C-deP, dephosphorylated HBc subunits.

FIG. 4A: Analyzed right after translation without additional incubation. FIG. 4B: Analyzed after additional overnight incubation following the end of translation. Rosc (Roscovitine)—250 µM, CDK2I (CDK2 inhibitor III)—250 µM, ERKI (Erk inhibitor II)—310 µM, Bisindo (Bisindolymaleimide I)—40 µM. Lanes 16-20 in FIG. 4A represent a shorter exposure of the lanes 1-5 of the agarose gel. C, full-length HBc protein; Ca, native capsids; C149, C-terminally truncated HBc protein (terminated at position 149); C-deP, dephosphorylated HBc subunits.

FIGS. 5A and 5C: $^{35}$S signals detected by autoradiography (lanes 1-14). FIG. 5B: Core proteins were also detected by the mAb against the core N-terminal sequence. OA (okadaic acid) was added to 50 nM in A and B. OA concentrations as indicated in C. FIGS. 5A and 5B, lanes 1, 2, 3, 7, 11, loaded right after translation; other lanes in FIGS. 5A and 5B and all lanes in FIG. 5C, loaded after overnight incubation at 37° C., with no inhibitor or the indicated inhibitors. C: full-length HBc protein; Ca, native capsids; C-deP, dephosphorylated HBc subunits.

FIG. 8C, lanes 2, 3) or E. coli (FIG. 8B, lanes 5-12; FIG. 8C, lane 4) were resolved on an agarose gel and detected by Spyro Ruby staining (FIG. 8B, top) and their associated nucleic acid by Sybr Gold staining (FIG. 8B, bottom). In addition, nucleic acid from the purified capsids was isolated and resolved on an agarose gel and detected by Sybr Gold staining (FIG. 8C). The RNA marker and tRNA were also loaded as size standards (FIG. 8C, lanes 1 and 5, respectively).

FIGS. 9A and 9B show the analysis of HBc expression and capsid assembly in mammalian cells. The indicated WT and mutant HBc expression constructs were transfected into HepG2 (FIG. 9A, lanes 1-4) or HEK289T (FIG. 9A, lanes 5-8; FIG. 9B, lanes 1-3) cells. Cytoplasmic lysate was resolved on an agarose gel and transferred to nitrocellulose membrane, and capsids (Ca) were detected by anti-HBc antibody (FIGS. 9A and 9B, top). The lysate was also resolved by SDS-PAGE and the core subunits (C— full-length or WT, C149, C149-4R) detected by Western blotting using anti-HBc antibody (FIG. 9A, middle and bottom; FIG. 9B, bottom).

DETAILED DESCRIPTION

The HBc CTD is thought to undergo dynamic phosphorylation and dephosphorylation events that regulate its nucleic acid binding, subcellular localization, and HBc functions in pgRNA packaging and DNA synthesis (Machida A, et al. (1991). *J Virol* 65: 6024-6030; Kann M, Gerlich W H (1994). *J Virol* 68: 7993-8000; Basagoudanavar S H, et al., (2007). *J. Virol.* 81:1641-1649; Perlman D H, et al., (2005). *Proc. Natl. Acad. Sci.* USA 102:9020-9025; Gazina E V, et al., (2000). *J Virol* 74: 4721-4728; Lan Y T, et al., (1999). *Virology* 259: 342-348; Liao W, Ou J H (1995). *J Virol* 69:1025-1029; Lewellyn E B, Loeb D D (2011). *PLoS One* 6: e17202). Liu, et al., *J Virol,* 89: 2918-2930, 2015. The nonspecific RNA binding activity of CTD allows incorporation of non-specific RNAs into capsids assembled in vitro or in bacteria (Porterfield J Z, et al. (2010). *J Virol* 84: 7174-7184). How or if capsid assembly discriminates the specific viral pgRNA vs. nonspecific RNAs during viral replication remains to be elucidated. It is known, however, that CTD phosphorylation is required for specific viral RNA packaging (Gazina E V, et al., (2000). *J Virol.* 74: 4721-4728; Lan Y T, et al., (1999), *Virology* 259: 342-348; Jung J, et al., (2014). *J Virol* 88: 8754-8767). Also, in insect or mammalian cells where CTD is phosphorylated, HBV capsids assembled from full-length HBc with intact CTD do not appear to package non-specific RNA (Lanford R E, Notvall L (1990). *Virology* 176:222-233; Hilditch C M, et al., (1990). *J Gen Virol.* 71 (Pt 11): 2755-2759; Ning X, et al., (2011). *PLoS Pathogens* 7: e1002255), in contrast to those assembled in bacteria where HBc is un-phosphorylated. These observations are consistent with the inhibition of CTD RNA binding by its phosphorylation.

Figure 1A:
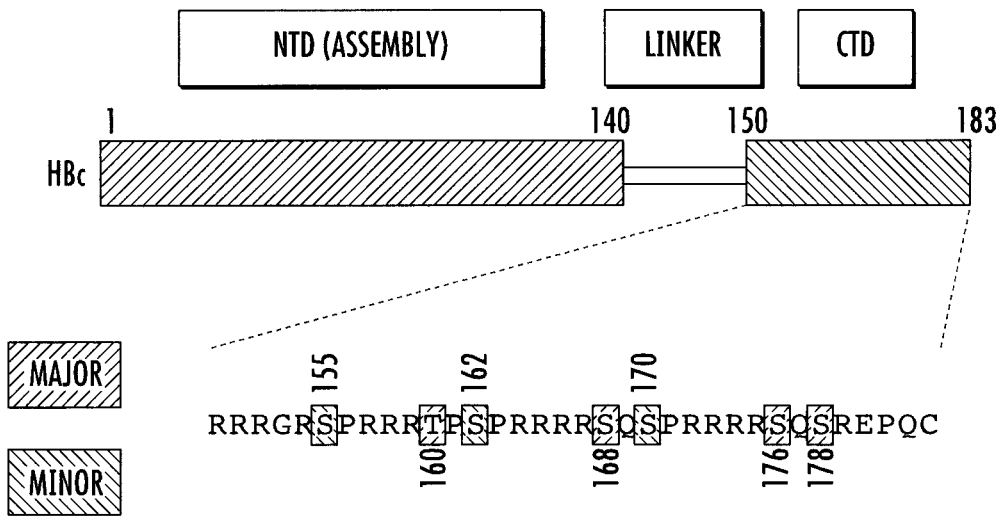
FIGS. 1A, 1B show the expression of WT and mutant HBc proteins in RRL.
Figure 1B:
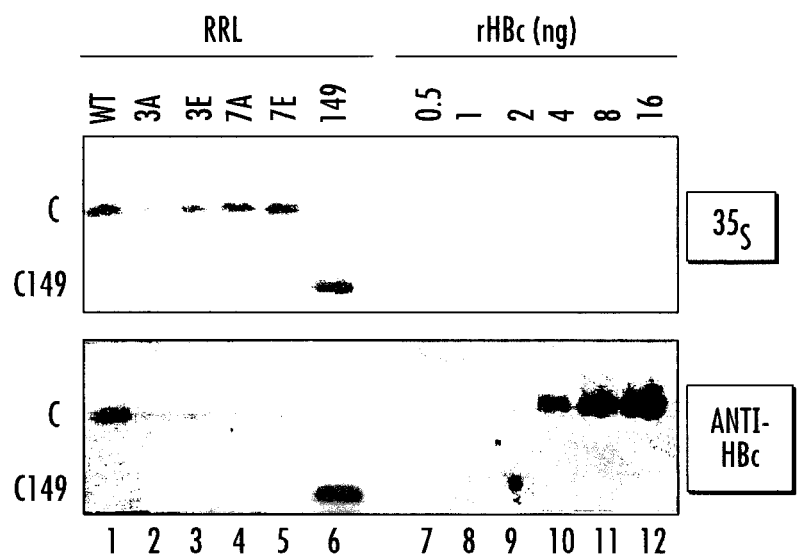

HBc contains three major S phosphorylation sites (S155, S162, and S170) Liao W, Ou J H, *J Virol* 69:1025-1029. Ludgate L, et al., (2011). *PLoS One* 6: e29566; Ludgate L, et al., (2012). *J Virol* 86: 12237-12250) and three additional Sff phosphorylation sites (T160, S168, and S176) have recently been identified (FIG. 1B). Besides these six known phosphorylation sites, another potential CTD phosphorylation site (S178) (FIG. 1B) is also conserved among most HBV isolates. Liu, et al., *J Virol,* 89: 2918-2930, 2015. As the virus does not encode any protein kinase, CTD phosphorylation is mediated exclusively by host kinases, including the cyclin-dependent kinase 2 (CDK2) and protein kinase C (PKC). To date, no information is available on the cellular phosphatase(s) that mediate CTD dephosphorylation, which accompanies viral reverse transcription and is required during the $2^{nd}$ strand DNA synthesis in duck HBV (DHBV), presumably to maintain the interior charge balance as more negative charges inside the NC builds up due to the conversion of the single-stranded pgRNA to the double-stranded DNA (Le Pogam S, et al., (2005). *J Virol* 79: 1871-1887; Chua P K, et al., (2010). *J Virol* 84: 2340-2351; Nguyen D H, Hu J (2008). *J Virol* 82: 6852-6861). S. Basagoudanavar, D. Perlman, and J. Hu. 2007. *J Virol,* 81:1641-1649.

The cell-free translation and assembly systems embodied herein allows for capsid assembly under cell-free conditions that also mimic the physiological salt and protein concentrations. Furthermore, the system recapitulates the dynamic post-translational modifications, most notably the phosphorylation and dephosphorylation of the capsid protein, which modulates capsid assembly. In embodiments, the methods utilize the C-terminal domain (CTD) and N-terminal domain (NTD) of the capsid protein in capsid assembly. Uses of the system include the screening of potential therapeutic agents which target these domains and inhibit capsid assembly and other functions of these domains in viral replication. The role of host factors in HBV capsid assembly would be targets for identifying inhibitors which block capsid assembly.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used in this specification and the appended claims, the term "or" is generally employed in its sense including "and/or" unless the content clearly dictates otherwise.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value or range. Alternatively, particularly with respect to biological systems or processes, the term can mean within an order of magnitude, preferably within 5-fold, and also preferably within 2-fold, of a value. Where particular values are described in the application and claims, unless otherwise stated the term "about" meaning within an acceptable error range for the particular value should be assumed.

"Optional" or "optionally" means that the subsequently described event or circumstance can or cannot occur, and that the description includes instances where the event or circumstance occurs and instances where it does not.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

As used herein, the terms "agent" or "pharmaceutically active agent" are meant to encompass any molecule, chemical entity, composition, drug, therapeutic agent, chemotherapeutic agent, diagnostic or biological agent capable of diagnosing, preventing, ameliorating, or treating a disease or other medical condition. The term includes small molecule compounds, host factors, cellular factors, hormones, enzymes, cytokines, antisense reagents, siRNA reagents, antibodies, enzymes, peptides organic or inorganic molecules, natural or synthetic compounds, chemotherapeutics, anti-virals, toxins, radiotherapeutics, radiosensitizing agents, gene therapy vectors, antisense nucleic acid constructs or small interfering RNA, kinase inhibitors, kinases, imaging agents, diagnostic agents, agents known to interact with an intracellular protein, polypeptides, and polynucleotides and the like. An agent can be assayed in accordance with the methods of the invention at any stage during clinical trials, during pre-trial testing, or following FDA-approval.

The term "hepatitis virus" is intended to include all of the hepatitis virus family, e.g., hepatitis A, hepatitis B, hepatitis C, etc. The term is also meant to cover all strains, types, subtypes and genotypes of the virus. In preferred embodiments, the hepatitis virus is hepatitis B virus (HBV).

The terms "C-terminal Domain (CTD)" or "C-terminal Domain (CTD) molecule(s)" are used interchangeably herein and are meant to include, without limitation, nucleic acids, polynucleotides, oligonucleotides, sense and antisense polynucleotide strands, complementary sequences, peptides, polypeptides, proteins, homologous and/or orthologous C-terminal Domain (CTD) molecules, isoforms, precursors, mutants, variants, derivatives, splice variants, alleles, different species, and active fragments thereof.

The terms "N-terminal Domain (NTD)" or "N-terminal Domain (NTD) molecule(s)" are used interchangeably herein and meant to include, without limitation, nucleic acids, polynucleotides, oligonucleotides, sense and antisense polynucleotide strands, complementary sequences, peptides, polypeptides, proteins, homologous and/or orthologous N-terminal Domain (NTD) molecules, isoforms, precursors, mutants, variants, derivatives, splice variants, alleles, different species, and active fragments thereof.

As used herein, the terms "nucleic acid sequence", "polynucleotide," and "gene" are used interchangeably throughout the specification and include complementary DNA (cDNA), linear or circular oligomers or polymers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. A "polynucleotide" means a single strand or parallel and anti-parallel strands of a nucleic acid. Thus, a polynucleotide may be either a single-stranded or a double-stranded nucleic acid. Polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. The nucleic acid sequences may be "chimeric," that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide. These sequences typically comprise at least one region wherein the sequence is modified in order to exhibit one or more desired properties.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-($C_3$-$C_6$)-alkynylcytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence. A variant, for example, may include conservative amino acid substitutions, as defined in the art, or nonconservative substitutions, providing that at least e.g. 10%, 25%, 50%, 75% or 90% of the activity of the original peptide, polypeptide or protein is retained. Also included are CTD and/or NTD molecules, fragments or variants having post-translational modifications such as sumoylation, phosphorylation glycosylation, splice variants, and the like, all of which may affect the efficacy of CTD and NTD functions.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

As used herein, unless otherwise indicated, the terms "peptide", "polypeptide" or "protein" are used interchangeably herein, and refer to a polymer of amino acids of varying sizes. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or be naturally occurring. This term also includes polypeptides that have been modified or derivatized, such as by glycosylation, acetylation, phosphorylation, and the like.

As used herein, the term "fragment" refers to an amino acid sequence which is shorter than the peptide from which it is derived, but which retains biological activity substantially similar to that of the original peptide. Such a fragment is at least two amino acids in length.

As used herein, the term "analog" refers to variations in the amino acid sequences of the peptides, which may typically include analogs that differ only by one to about four amino acid changes. Other examples of analogs include peptides with minor amino acid variations from the peptides exemplified herein. In particular, peptides containing conservative amino acid replacements, i.e., those that take place within a family of amino acids that are related in their side chains, constitute analogs. "Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.,* 25(22), 4429-4443, Toulme, J. J., (2001) *Nature Biotechnology* 19:17-18; Manoharan M., (1999) *Biochemica et Biophysica Acta* 1489:117-139; Freier S. M., (1997) *Nucleic Acid Research,* 25:4429-4443, Uhlman, E., (2000) *Drug Discovery & Development,* 3: 203-213, Herdewin P., (2000) *Antisense & Nucleic Acid Drug Dev.,* 10:297-310); 2'-O, 3'-C-linked [3.2.0] bicycloarabinonucleosides (see e.g. N. K Christiensen, et al, (1998) *J. Am. Chem. Soc.,* 120: 5458-5463; Prakash T P, Bhat B. (2007) *Curr Top Med. Chem.* 7(7):641-9; Cho E J, et al. (2009) *Annual Review of Analytical Chemistry,* 2, 241-264). Such analogs include synthetic nucleotides designed to enhance binding properties, e.g., duplex or triplex stability, specificity, or the like.

The term "homolog" includes peptide fragments which share at least 60 percent identity at the amino acid level, and preferably 75 percent identity, and substantially similar biological activity to a reference peptide. These preferred percentages reflect the small size of the peptides.

The term "percent sequence identity" or having "a sequence identity" refers to the degree of identity between any given query sequence and a subject sequence.

A "label" or a "detectable label" is a composition detectable by spectroscopic, photochemical, biochemical, immunochemical, chemical or any other means. For example, useful labels include radio labeled molecules, fluorophores, luminescent compounds, electron-dense reagents, enzymes (e.g., as commonly used in an ELISA), biotin, digoxigenin, or haptens and proteins which can be made detectable, e.g., by incorporating a label into the peptide or used to detect antibodies specifically reactive with the peptide.

The term "high-throughput screening" or "HTS" refers to a method drawing on different technologies and disciplines, for example, optics, chemistry, biology or image analysis to permit rapid, highly parallel biological research and drug discovery. HTS methods are known in the art and they are generally performed in multiwell plates with automated liquid handling and detection equipment; however it is envisioned that the methods of the invention may be practiced on a microarray or in a microfluidic system.

As used herein, the term "target" or "target molecule" refers to any type of molecule, or structure to be detected, characterized or to which a ligand specifically binds to. The molecule can be an intracellular molecule, such as for example, nucleic acid sequences, peptides, structures (e.g. intracellular membranes, ribosomes, etc.), surface molecules (e.g. receptors), extracellular molecules (e.g. cytokines, enzymes, viral particles, organisms, biological samples and the like.

The term "encapsulation," or "encapsulated," as used herein refers to the envelopment of a heterologous substance, such as a heterologous nucleic acid, within the hepatitis virus (e.g. HBV) capsids defined herein.

The terms "patient" or "individual" or "subject" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests. For example the term "treat" or "treating" with respect to tumor cells refers to stopping the progression of said cells, slowing down growth, inducing regression, or amelioration of symptoms associated with the presence of said cells. Treatment of an individual suffering from an infectious disease organism refers to a decrease and elimination of the disease organism from an individual. For example, a decrease of viral particles as measured by plaque forming units or other automated diagnostic methods such as ELISA etc.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention.

As defined herein, a "therapeutically effective amount" of a compound (i.e., an effective dosage) means an amount sufficient to produce a therapeutically (e.g., clinically) desirable result. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Capsid Assembly/Disassembly

Multiple subunits of the hepatitis B virus (HBV) core or capsid (HBc) protein assemble into an icosahedral capsid that packages the viral pregenomic RNA (pgRNA). The N-terminal domain (NTD) of HBc is sufficient to assemble into icosahedral capsid, in the absence of pgRNA or any other viral factors, in overexpression systems and in vitro, whereas CTD is deemed dispensable for capsid assembly but essential for pgRNA packaging. The examples section which follows, describes that HBc expressed in a mammalian cell lysate, the rabbit reticulocyte lysate (RRL), was able to assemble into capsids even though the subunit concentrations (low nM), mimicking those achieved under conditions of viral replication, were far below those required for capsid assembly in vitro. With (physiologically) low subunit concentrations, NTD was insufficient for capsid assembly and CTD was also required, both in RRL and in mammalian cells. The highly basic CTD likely facilitated assembly under these conditions by interactions with non-specific RNA, which was packaged into capsids. CTD likely also mediated protein-protein interactions which, along with CTD-RNA interactions, effectively lowered the threshold HBc concentration required for capsid assembly. Furthermore, CTD underwent phosphorylation and dephosphorylation events in RRL as occurring in vivo, which modulated capsid assembly. The cyclin-dependent kinase 2 (CDK2) was identified as partially responsible for CTD phosphorylation in RRL and shown to be incorporated into capsids, as occurring in vivo. Furthermore, for the first time, a cellular protein phosphatase, PP2A, was identified as a putative phosphatase responsible for CTD dephosphorylation. These results have important implications for HBV assembly during replication and provide a cell-free system to further study host modulation of capsid assembly.

Embodiments of the invention are directed, inter alia, to methods of identifying agents for inhibiting Hepatitis virus capsid assembly and/or promoting/inducing capsid disassembly. In preferred embodiments, the hepatitis virus is hepatitis B virus (HBV). Other viruses include, arbovirus, lentiviruses and the like, In preferred embodiments the composition is a cell-free composition. The cell free system can comprise various components, such as, for example, one or more transcription factors, translation factors, proteins, chaperones, detectable labels, or combinations thereof.

Without limiting the invention in any way, the term "hepatitis B virus" will be used for brevity, however, it is to be understood that the invention is applicable to other virus groups or families. In one embodiment, the method comprises contacting a composition having one or more hepatitis B virus C-terminal Domain (CTD) and N-terminal Domain (NTD) nucleic acids, polynucleotides, oligonucleotides proteins, peptides, mutants or fragments thereof, with one or more candidate therapeutic compounds. In one embodiment, the HBV C-terminal Domain (CTD) nucleic acid sequence comprises one or more mutations, variants, homologs, analogs or combinations thereof. In another embodiment, the hepatitis B virus C-terminal Domain (CTD) amino acid sequence comprises one or more mutations, variants, homologs, analogs or combinations thereof. In another embodiment, the hepatitis B virus N-terminal Domain (NTD) nucleic acid sequence comprises one or more mutations, variants, homologs, analogs or combinations thereof. In another embodiment, the hepatitis B virus N-terminal Domain (NTD) amino acid sequence comprises one or more mutations, variants, homologs, analogs or combinations thereof.

In one embodiment the NTD and/or the CTD molecules are chimeric. For example, the molecule may comprise one or more ribonucleotides and deoxyribonucleotides. In another example, one nucleobase may be a locked nucleic acid (LNA) or peptide nucleic acid.

In certain embodiments, a Hepatitis B virus capsid (HBc) molecule comprises an N-terminal domain (NTD) molecule, a C-terminal domain (CTD) molecule, fragments, mutants, variants or combinations thereof. In some embodiments, the HBc further comprises a linker molecule linking the NTD and CTD molecules. In some embodiments, the NTD or CTD molecules are optionally truncated at an N-terminal end or C-terminal end or at both N-terminal and C-terminal ends. In some embodiments, wherein the NTD and CTD molecules are oligonucleotides or polynucleotides. In certain embodiments, the CTD molecules further comprise one or more nucleobase mutations, substitutions, insertions, deletions, variants, analogs, or combinations thereof. The one or more nucleobase mutations, substitutions, insertions, deletions, analogs or variants thereof, can in some embodiments occur at one or more CTD phosphorylation sites comprising S155, S162, S170, T160, S168, S176 or S178. In another embodiment, the Hepatitis B virus capsid molecules are peptides or polypeptides. Amino acid sequences encoding NTD and/or CTD peptides or polypeptides further comprise one or more mutants, deletions, insertions, substitutions, variants or combinations thereof.

The invention is intended to encompass expression vectors which may encode or express one or more CTD or NTD molecules. Accordingly, a composition may comprise combinations of CTD and NTD molecules.

In an embodiment, an expression vector encodes a hepatitis B virus N-terminal Domain (NTD) nucleic acid sequence. In another embodiment, an expression vector encodes a nucleic acid sequence comprising a hepatitis B virus N-terminal Domain (NTD) nucleic acid sequence having a sequence identity of at least about 50% with a wild type NTD sequence. In other embodiments, an expression vector encodes a nucleic acid sequence comprising at least about 75%, 80%, 85%, 90%, 95%, 96%, 97%, 98%, 99% sequence identity with an NTD wild type sequence.

In an embodiment, an expression vector encodes a hepatitis B virus C-terminal Domain (CTD) nucleic acid sequence. In another embodiment, an expression vector encodes a nucleic acid sequence comprising a hepatitis B virus C-terminal Domain (CTD) nucleic acid sequence having a sequence identity of at least about 50% with a wild type CTD sequence. In other embodiments, an expression vector encodes a nucleic acid sequence comprising at least about 75%, 80%, 85%, 90%, 95%, 96%, 97%, 98%, 99% sequence identity with a CTD wild type sequence.

In an embodiment, an expression vector encodes a hepatitis B virus N-terminal Domain (NTD) and a hepatitis B virus C-terminal Domain (CTD) nucleic acid sequence. In another embodiment, an expression vector encodes a nucleic acid sequence comprising a hepatitis B virus NTD and CTD nucleic acid sequence wherein the NTD has a sequence identity of at least about 50% with a wild type NTD and/or the CTD has a sequence identity of at least about 50% with a wild type CTD sequence. In other embodiments, an expression vector encodes a nucleic acid sequence comprising a hepatitis B virus NTD and CTD nucleic acid sequence wherein the NTD and/or CTD sequences having at least about 75%, 80%, 85%, 90%, 95%, 96%, 97%, 98%, 99% sequence identity with an NTD and/or CTD wild type sequence, respectively.

In another embodiment, a nucleic acid sequence comprises a hepatitis B virus N-terminal Domain (NTD) nucleic acid sequence having a sequence identity of at least about 50% with a wild type NTD sequence. In other embodiments, a nucleic acid sequence comprises a hepatitis B virus N-terminal Domain (NTD) nucleic acid sequence having a sequence identity of at least about 75%, 80%, 85%, 90%, 95%, 96%, 97%, 98%, 99% sequence identity with an NTD wild type sequence.

In another embodiment, a nucleic acid sequence comprises a hepatitis B virus C-terminal Domain (CTD) nucleic acid sequence having a sequence identity of at least about 50% with a wild type CTD sequence. In other embodiments, a nucleic acid sequence comprises a hepatitis B virus C-terminal Domain (CTD) nucleic acid sequence having a sequence identity of at least about 75%, 80%, 85%, 90%, 95%, 96%, 97%, 98%, 99% sequence identity with an CTD wild type sequence.

In an embodiment, an expression vector encodes a hepatitis B virus N-terminal Domain (NTD) and a hepatitis B virus C-terminal Domain (CTD) nucleic acid sequence. In another embodiment, an expression vector encodes a nucleic acid sequence comprising a hepatitis B virus NTD and CTD nucleic acid sequence wherein the NTD has a sequence identity of at least about 50% with a wild type NTD and/or the CTD has a sequence identity of at least about 50% with a wild type sequence. In other embodiments, an expression vector encodes a nucleic acid sequence comprising a hepatitis B virus NTD and CTD nucleic acid sequence wherein the NTD and/or CTD sequences having at least about 75%, 80%, 85%, 90%, 95%, 96%, 97%, 98%, 99% sequence identity with an NTD and/or CTD wild type sequence, respectively.

Modified or Mutated Nucleic Acid Sequences:

In some embodiments, any of the NTD and CTD nucleic acid sequences may be modified or derived from a native nucleic acid sequence, for example, by introduction of mutations, deletions, substitutions, modification of nucleobases, backbones and the like. Examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments, modified oligonucleotides comprise those with phosphorothioate backbones and those with heteroatom backbones, $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH,). The amide backbones disclosed by De Mesmaeker et al. *Acc. Chem. Res.* 1995, 28:366-374) are also embodied herein. In some embodiments, the nucleic acid sequences having morpholino backbone structures (Summerton and Weller, U.S. Pat. No. 5,034,506), peptide nucleic acid (PNA) backbone wherein the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). The nucleic acid sequences may also comprise one or more substituted sugar moieties. The nucleic acid sequences may also have sugar mimetics such as cyclobutyls in place of the pentofuranosyl group.

The nucleic acid sequences may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentiobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-77; Gebeyehu, G., et al. *Nucl. Acids Res.* 1987, 15:4513). A "universal" base known in the art, e.g., inosine may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278).

Another modification of the nucleic acid sequences of the invention involves chemically linking to the nucleic acid sequences one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci.* USA 1989, 86, 6553), cholic acid (Manoharan et al. *Bioorg. Med. Chem. Let.* 1994, 4, 1053), a thioether, e.g., hexyl-S-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651).

It is not necessary for all positions in a given nucleic acid sequence to be uniformly modified, and in fact more than one of the aforementioned modifications may be incorporated in a single nucleic acid sequence or even at within a single nucleoside within a nucleic acid sequence.

The isolated nucleic acid molecules of the present invention can be produced by standard techniques. For example, polymerase chain reaction (PCR) techniques can be used to obtain an isolated nucleic acid containing a nucleotide sequence described herein. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

In some embodiments, the nucleic acids described herein, e.g., vectors, nucleic acids encoding an NTD and/or CTD polypeptide or active fragment thereof, can be incorporated into a gene construct.

NTD, CTD Polypeptides and Proteins:

In some embodiments, the NTD, CTD molecule is a polypeptide.

NTD, CTD polypeptides can be generated using recombinant techniques or using chemical synthesis. Methods for generating such polypeptides, and methods required for the purification of such polypeptides, are known in the art, see, e.g., Sambrook, Molecular Cloning: A Laboratory Manual (CSHL Press, $3^{rd}$ Edition, 2001).

Modifications can be made to a protein to alter the pharmacokinetic properties of the protein to make it more suitable for use in protein therapy. For example, such modifications can result in longer circulatory half-life, an increase in cellular uptake, improved distribution to targeted tissues, a decrease in clearance and/or a decrease of immunogenicity. A number of approaches useful to modify a polypeptide, peptide or peptide mimetic are known in the art, including chemical modification.

Candidate Therapeutic Agents

The methods embodied herein, identify candidate therapeutic agents that would be of importance in preventing or treating hepatitis virus infections (e.g. HBV), by, for example, inhibiting assembly of the capsid and/or inducing or promoting capsid disassembly. In other embodiments, a candidate therapeutic agent modulates expression, function, activity of various molecules, such as for example, RNA binding activity, DNA-binding activity, protein binding activity and/or modulates the phosphorylation/dephosphorylation of CTD and/or NTD molecules. In preferred embodiments, the method is a high-throughput screening (HTS) assay.

Potential pharmaceutically active agents are discoverable based on their ability to modulate capsid assembly/disassembly. Accordingly, in an embodiment, a method for modulating Hepatitis B virus capsid assembly/disassembly in vitro comprises transcribing, translating or expressing one or more C-terminal Domain (CTD) molecules and/or one or more N-terminal domain (NTD) molecules, the CTD and NTD molecules comprising nucleic acids, polynucleotides, oligonucleotides proteins, peptides, mutants or fragments thereof, in a cell-free system, and contacting the system with one or more wherein a candidate therapeutic agents. A candidate therapeutic agent is identified by a variety of effects such as for example, inhibiting assembly and/or inducing or promoting disassembly of the capsid, modulates the expression, function, activity, RNA binding activity, DNA-binding activity, protein binding activity and/or modulates the phosphorylation/dephosphorylation of CTD and/or NTD molecules, or any other functions attributed to the capsid protein, especially, the C-terminal domain.

The methods encompass assembly of hepatitis B virus capsids. In one embodiment a method for assembling Hepatitis B virus capsids in vitro comprises transcribing, translating or expressing one or more C-terminal Domain (CTD) and N-terminal domain (NTD) nucleic acids, polynucleotides, oligonucleotides proteins, peptides, mutants or fragments thereof, in a cell-free system.

It may be desirable to assemble capsids which either contain a pharmaceutically active agent either within the capsid or bound to the surface of a capsid. Accordingly, in some preferred embodiments, one or more agents can be encapsulated in the Hepatitis B virus capsid either during assembly or any time thereafter. These agents could be, for example, therapeutic agents, diagnostic agents and the like. Examples include without limitation: chemotherapeutic agents, anti-virus agents, anti-inflammatory agents, nucleic acids, vectors, expression vectors, polynucleotides, oligonucleotides, proteins, peptides, lipids, lipoproteins, organic molecules, inorganic molecules, synthetic compounds, natural compounds, saccharides, or combinations thereof. The agents can also be selected from a variety of known classes of drugs, including, for example, analgesics, anesthetics, anti-inflammatory agents, anthelmintics, anti-arrhythmic agents, antiasthma agents, antibiotics (including penicillins), anticancer agents (including Taxol), anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radiopharmaceuticals, hormones, sex hormones (including steroids), time release binders, anti-allergic agents, stimulants and anoretics, steroids, sympathomimetics, thyroid agents, vaccines, vasodilators, and xanthines.

Any additional pharmaceutically active agents need not be therapeutic agents. For example, the agent may be cytotoxic to the local cells to which it is delivered but have an overall beneficial effect on the subject. Further, the agent may be a diagnostic agent with no direct therapeutic activity per se, such as a contrast agent for bioimaging.

In embodiments, the assembled hepatitis B virus capsid is non-replicating. The capsid itself can enter a cell, much like the native HBV, for delivery of an encapsulated agent. In some embodiments, the capsid is pseudotyped, or can comprise ligands which specifically bind to target molecules in vitro or in vivo. Accordingly, the assembled capsid can be specifically targeted in vitro or in vivo for therapeutic and diagnostic purposes, e.g. delivery of a therapeutic agent to a specific cell or organ. Diagnostically the capsid could either itself be labeled with a detectable label or the detectable label is encapsulated within the capsid.

In one embodiment, the ligands comprise: polypeptides such as antibodies or antibody fragments bearing epitope recognition sites, such as Fab, Fab', F(ab')$_2$ fragments, Fv fragments, single chain antibodies, antibody mimetics (such as DARPins, affibody molecules, affilins, affitins, anticalins, avimers, fynomers, Kunitz domain peptides and monobodies), peptoids, aptamers and the like. In some embodiments, the ligands comprise: antibodies, antibody fragments, Fv fragments; single chain Fv (scFv) fragments; Fab' fragments; F(ab')2 fragments, humanized antibodies and antibody fragments; camelized antibodies and antibody fragments, human antibodies and antibody fragments, monospecific or bispecific antibodies, disulfide stabilized Fv fragments, scFv tandems ((scFv) fragments), diabodies, tribodies or tetrabodies, peptoids, peptide or nucleic acid aptamers, antibody mimetics or combinations thereof. In other embodiments, the ligands comprise: a polypeptide, antibodies, antibody fragments, antibody mimetics, single chain antibodies, nucleic acids, an aptamer, a peptoid or a sugar moiety or combinations thereof. In certain embodiments, the ligands are peptide or nucleic acid aptamers. In other embodiments, the ligands are sugar moieties comprising glycosaminoglycans, heparan sulfates or chondroitin sulfates.

Compositions and Modulators of Hepatitis Virus Capsid Assembly/Disassembly.

As mentioned, hepatitis B virus (HBV) remains an important global pathogen that chronically infects hundreds of millions of people worldwide and causes hepatitis, cirrhosis and liver cancer (Trepo C., et al. (2014). *Lancet*, 384(9959): 2053-2063). HBV is enveloped virus with an inner capsid shell, which in turn encloses a small (3.2 kbp) DNA genome. It would be of importance to identify agents which prevent capsid assembly or induce or promote capsid disassembly of the hepatitis B virus that could be used to prevent and treat infections and associated disorders. The methods embodied herein allow for the identification of candidate therapeutic agents which modulate hepatitis B virus capsid assembly, thereby preventing and treating a hepatitis B virus infection.

In a preferred embodiment, a pharmaceutical composition comprises an inhibitor of hepatitis virus, e.g. hepatitis B virus, capsid assembly. In another preferred embodiment, a pharmaceutical composition comprises a plurality of inhibitors of hepatitis B virus capsid assembly in one or more dose concentrations. In another preferred embodiment, a composition comprises at least one inhibitor of hepatitis B virus capsid assembly and at least one other therapeutic agent. For example, the second therapeutic agent may be one that treats a particular symptom. In another example, the agent targets another aspect of the disease, such as for example, in the case of a tumor, abnormal cell proliferation. In this case the agent would be a chemotherapeutic agent used in treating a cancer patient.

In a preferred embodiment, a pharmaceutical composition comprises an inducer or promoter of virus capsid disassembly, e.g. hepatitis B virus capsid. In another preferred embodiment, a pharmaceutical composition comprises a plurality of inducers or promoters of hepatitis B virus capsid disassembly in one or more dose concentrations. In another preferred embodiment, a composition comprises at least one inducer or promoter of hepatitis B virus capsid disassembly and at least one other therapeutic agent.

In preferred embodiments, a composition comprises a modulator of hepatitis B virus capsid assembly. Preferably, the modulator inhibits the assembly of the capsid, inhibits viral replication, modulates the expression, function, activity, RNA binding activity, DNA-binding activity, protein binding activity and/or modulates the phosphorylation/dephosphorylation of CTD and/or NTD molecules, or any other functions attributed to the capsid protein, especially, the C-terminal domain. In another preferred embodiment, a composition comprises a modulator of hepatitis B virus capsid disassembly.

In a preferred embodiment, a method of treating a patient suffering from a hepatitis virus infection or at risk of being infected by hepatitis virus, comprises administering to a patient in need thereof, a therapeutically effective amount of an inhibitor of hepatitis virus capsid assembly.

Modulators of Hepatitis Virus Capsid Assembly/Disassembly:

In preferred embodiments, a method of identifying a modulator of hepatitis virus (e.g. hepatitis B virus) capsid assembly or disassembly comprises contacting a biological sample with a test agent and measuring the expression, function, activity, RNA binding activity, DNA-binding activity, protein binding activity and/or the state of phosphorylation/dephosphorylation of CTD and/or NTD molecules in the biological sample. In certain embodiments, a test agent is identified as an inhibitor of hepatitis virus (e.g. hepatitis B virus) capsid assembly when the test agent fails to assemble in the presence of the test agent. In other embodiments, a test agent is identified as an inducer or promoter of, for example, hepatitis B virus capsid disassembly when the capsid disintegrates or degrades in the presence of the test agent, thereby inhibiting the virus from infecting a host cell, or inhibits the replication of the virus. In other embodiments, a test agent is identified as an inducer or promoter of, for example, hepatitis B virus capsid assembly. The assembled capsids may comprise one or more therapeutic and/or diagnostic agents. The candidate agents can be screened which modulate these desired functions or activities. One of skill in the art could use any method for identifying an assembled or disassembled capsid and the extent of assembly or disassembly. The examples section which follows describes some of these methods in detail.

The biological samples may be obtained from a patient, e.g. cells, fluids etc. The sample can also be synthetic, e.g. peptides, oligonucleotides etc. The sample can also be a transformed cell, a cell transduced with a vector expressing a desired molecule etc. Thus, in embodiments, a biological sample comprises: fluids, peptides, polypeptides, oligonucleotides, polynucleotides, cells, tissues or combinations thereof.

A wide variety of agents can be used to target hepatitis virus capsid assembly and any associated molecules. For example, the associated molecules can be any molecule that is involved in the mechanism of capsid assembly and can be upstream or downstream in the pathway. In certain embodiments, the agent is a host factor. For example, an enzyme for phosphorylating or dephosphorylating a CTD and/or NTD molecule; a cytokine, hormones, proteins, peptides, or any other host factor.

Small Molecules:

Another example of an agent is a small molecule. In order to identify, small molecules as modulators of hepatitis virus capsid assembly, small molecule test compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio., 1:60 (1997). In addition, a number of small molecule libraries are commercially available.

Small molecules may include cyclical carbon or heterocyclic structures and/or aromatic or polyaromatic structures substituted with one or more of the above functional groups. Also of interest as small molecules are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc. to produce structural analogs.

As such, the small molecule may be obtained from a library of naturally occurring or synthetic molecules, including a library of compounds produced through combinatorial means, i.e., a compound diversity combinatorial library. Combinatorial libraries, as well as methods for the production and screening, are known in the art.

Chemical Libraries:

Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, Chem Rev 96:555-600, 1996; Kenan et al., Exploring molecular diversity with combinatorial shape libraries, Trends Biochem Sci 19:57-64, 1994; Janda, Tagged versus untagged libraries: methods for the generation and screening of combinatorial chemical libraries, Proc Natl Acad Sci USA. 91:10779-85, 1994; Lebl et al., One-bead-one-structure combinatorial libraries, Biopolymers 37:177-98, 1995; Eichler et al., Peptide, peptidomimetic, and organic synthetic combinatorial libraries, Med Res Rev. 15:481-96, 1995; Chabala, Solid-phase combinatorial chemistry and novel tagging methods for identifying leads, Curr Opin Biotechnol. 6:632-9, 1995; Dolle, Discovery of enzyme inhibitors through combinatorial chemistry, Mol Divers. 2:223-36, 1997; Fauchere et al., Peptide and non-peptide lead discovery using robotically synthesized soluble libraries, Can J. Physiol Pharmacol. 75:683-9, 1997; Eichler et al., Generation and utilization of synthetic combinatorial libraries, Mol Med Today 1: 174-80, 1995; and Kay et al., Identification of enzyme inhibitors from phage-displayed combinatorial peptide libraries, Comb Chem High Throughput Screen 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., Proc. Nat. Acad. Sci. USA, 90:6909-6913 (1993)); vinylogous polypeptides (Hagihara, et al., J. Amer. Chem. Soc. 114:6568 (1992)); nonpeptidal peptidomimetics with β-D-glucose scaffolding (Hirschmann, et al., J. Amer. Chem. Soc., 114:9217-9218 (1992)); analogous organic syntheses of small compound libraries (Chen, et al., J. Amer. Chem. Soc., 116:2661 (1994)); oligocarbamates (Cho, et al., Science, 261:1303 (1993)); and/or peptidyl phosphonates (Campbell, et al., J. Org. Chem. 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., Nature Biotechnology, 14(3):309-314 (1996) and PCT/US96/10287); carbohydrate libraries (see, e.g., Liang, et al., Science, 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

Other Agents:

These can include any synthetic or natural peptides, glycoproteins, enzymes, modulators of signaling, modulators of phosphorylation, phosphatases, enzymes, hormones, inhibitors of assembly of transcription or translational factor complexes, organic or inorganic molecules and the like.

Microarrays:

Identification of an agent, for example, a nucleic acid sequence capable of modulating hepatitis virus capsid assembly and associated molecules involved in the capsid assembly e.g. CTD, NTD molecules, can be achieved by immobilizing a library of nucleic acids onto the substrate surface so that each unique nucleic acid is located at a defined position to form an array.

Microarrays may be prepared, used, and analyzed using methods known in the art (see, e.g., Brennan et al., 1995, U.S. Pat. No. 5,474,796; Schena et al., 1996, *Proc. Natl. Acad. Sci.* U.S.A. 93: 10614-10619; Baldeschweiler et al., 1995, PCT application WO95/251116; Shalon, et al., 1995, PCT application WO95/35505; Heller et al., 1997, *Proc. Natl. Acad. Sci.* U.S.A. 94: 2150-2155; and Heller et al., 1997, U.S. Pat. No. 5,605,662). In other embodiments, a microarray comprises peptides, or other desired molecules which can be assayed to identify a candidate agent.

The methods of screening of the invention comprise using screening assays to identify, from a library of diverse molecules, one or more compounds having a desired activity. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems such as for example, protein-protein interactions, enzyme catalysis, small molecule-protein binding, RNA binding activity, DNA-binding activity, protein binding activity. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000 and even up to about 100,000 to 1,000,000 different compounds a day using the integrated systems of the invention.

Typically in HTS, target molecules are administered or cultured in the cell-free systems which as described in detail in the examples which follow, including the appropriate controls.

In one embodiment, screening comprises contacting each cell-free culture system comprising a composition having one or more hepatitis B virus C-terminal Domain (CTD) and N-terminal Domain (NTD) nucleic acids, polynucleotides, oligonucleotides proteins, peptides, mutants or fragments thereof, with a diverse library of member compounds and measuring the expression, function, activity, RNA binding activity, DNA-binding activity, protein binding activity and/or the state of phosphorylation/dephosphorylation of CTD and/or NTD molecules. In embodiments, a test agent is identified as an inhibitor of hepatitis B virus capsid assembly when the fails to assemble in the presence of the test agent. In other embodiments, the test agent is identified as an inducer or promoter of hepatitis B virus capsid disassembly when the capsid disassembles, degrades, disintegrates or loses its normal structure due to, for example, degradation of one or more structural or functional molecules. The cell-free system can comprise combinations of one or more CTD and NTD molecules, CTD and NTD molecules linked by a linker, or any combination thereof. For example, in one embodiment, the method comprises contacting a composition having one or more hepatitis B virus C-terminal Domain (CTD) and N-terminal Domain (NTD) nucleic acids, polynucleotides, oligonucleotides proteins, peptides, mutants or fragments thereof, with one or more candidate therapeutic compounds. In one embodiment, the hepatitis B virus C-terminal Domain (CTD) nucleic acid sequence comprises one or more mutations, variants, homologs, analogs or combinations thereof. In another embodiment, the hepatitis B virus C-terminal Domain (CTD) amino acid sequence comprises one or more mutations, variants, homologs, analogs or combinations thereof. In another embodiment, the hepatitis B virus N-terminal Domain (NTD) nucleic acid sequence comprises one or more mutations, variants, homologs, analogs or combinations thereof. In another embodiment, the hepatitis B virus N-terminal Domain (NTD) amino acid sequence comprises one or more mutations, variants, homologs, analogs or combinations thereof.

In one embodiment the invention provides soluble assays using any of the molecules embodied herein. In another embodiment, the invention provides solid phase based in vitro assays in a high throughput format, where, for example, the test agent is attached to a solid phase substrate. In the high throughput assays of the invention, either soluble or solid state, it is possible to screen up to several thousand different modulators or ligands in a single day.

In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay many plates per day; assay screens for up to about 6,000, 20,000, 50,000, or more than 100,000 different compounds are possible using the integrated systems of the invention.

For a solid state reaction, an agent of interest, e.g., a modulator of phosphorylation/dephosphorylation can be bound to the solid state component, directly or indirectly, via covalent or non-covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selection family, and the like; see, e.g., Pigott & Power, The Adhesion Molecule Facts Book I (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The screening assays of the invention suitably include and embody, animal models, cell-based systems and non-cell based systems.

Administration of Compositions to Patients

In another embodiment, a method of preventing, treating, reducing, eradicating or inhibiting a hepatitis virus infection in a subject in need thereof, comprises administering to the subject a therapeutically effective amount of a compound or capsid comprising a therapeutic and/or diagnostic agent by the methods embodied herein. The compositions or agents identified by the methods described herein may be administered to animals including human beings in any suitable formulation. For example, the compositions for modulating protein degradation may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

The agents or compounds can be administered with one or more therapies. The chemotherapeutic agents may be administered under a metronomic regimen. As used herein, "metronomic" therapy refers to the administration of continuous low-doses of a therapeutic agent.

Dosage, toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED$_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC$_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a compound (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

Kits

In embodiments, a kit comprises an NTD molecule, a CTD molecule, a vector encoding an NTD and/or CTD molecule or any combinations thereof. As used herein, the term "kit" refers to any delivery system for delivering materials. Inclusive of the term "kits" are kits for both research and clinical applications. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides or liposomes. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, applicants do not admit any particular reference is "prior art" to their invention. Embodiments of inventive compositions and methods are illustrated in the following examples.

EXAMPLES

The following non-limiting examples are illustrative of the invention.

Example 1: Core Protein C-Terminal Domain-Dependent Hepatitis B Virus Capsid Assembly Regulated by Host-Mediated Modification It is reported here, in contrast to the overexpression systems and in vitro assembly reactions, the HBc CTD, in addition to NTD, is required to facilitate capsid assembly under conditions mimicking viral replication in mammalian cells and in mammalian cell lysate. Furthermore, it was discovered that CTD phosphorylation dynamics, as regulated by endogenous cellular kinases and phosphatases, can influence capsid assembly through the modulation of its RNA binding activity.

Materials and Methods

Plasmids: pCI-HBc, -HBc-3A, -HBc-3E, -HBc-7A, and -HBc-7E were constructed by inserting into the pCI vector (Promega) between the Nhe I and Sal 1 sites the WT or mutant HBc coding sequences, which were amplified by polymerase chain reaction (PCR) using primers containing the designated serine/threonine-to-alanine or glutamic acid substitutions and (FIG. 1A). pCIHBc-149 and -149RRRR ("RRRR" disclosed as SEQ ID NO: 2) were similarly constructed via PCR mutagenesis, which were used to express, respectively, HBc truncated at 149 and HBc truncated at 149 plus four Arg residues at the end. The pCI plasmids were used to express the HBc proteins both in mammalian cells as well as during in vitro transcription and translation.

In Vitro Translation in the Rabbit Reticulocyte Lysate:

The TNT Coupled Rabbit Reticulocyte Lysate (RRL) in vitro translation system (Promega) was used to express the HBc proteins as recommended by the manufacturer's protocol. In vitro translated proteins were labeled by $^{35}$S methionine. The translation reaction mix contained ca. 125 mM KCl and 2.5 mM Mg$^{++}$ (Promega).

In Vitro Capsid Assembly in RRL.

Unless specifically indicated otherwise, the general assembly reactions included 1 to 3 microL of translation products per 10 microL final reaction volume in 1× buffer 3 (100 mM NaCl, 50 mM Tris-HCl, 10 mM MgCl$_2$, 1 mM DTT, pH 7.9; New England Biolabs) supplemented with 1×EDTA-free protease inhibitor cocktail (Roche) and 0.8 U/µl RNasin Plus RNase Inhibitor (Promega). The reactions were incubated for 16 hrs at 37° C. unless indicated otherwise. Where indicated, additional enzymatic manipulations were performed using the same reaction buffer as above. (1) Exogenous phosphatase treatment. One unit of calf intestinal alkaline phosphatase (CIAP; New England Biolabs) per microliter of the final reaction volume was added at the end of translation and incubated for 16 hours at 37° C. (2) Kinase inhibitor treatment. Roscovitine, Cdk2 Inhibitor III, Erk Inhibitor II, and Bisindolymaleimide I (Bisindo) (all from Calbiochem and dissolved in dimethyl sulphoxide (DMSO)) were added to the reactions at the indicated concentrations just before translation and were again added during the 16 hr incubation at 37° C. following translation. The final concentration of DMSO in all reactions was 1% (i.e., kinase inhibitor stocks were always diluted 100-fold into the translation or assembly reactions). (3) Phosphatase inhibitor treatment. A cocktail of non-specific phosphatase inhibitors (10 mM NaF, 50 mM β-glycerophosphate, 10 mM sodium pyrophosphate, and 2 mM sodium orthovanadate; all final concentrations) were added at the end of the translation and incubated for 16 hours at 37° C. Alternatively, okadaic acid (Sigma) was added at the end of the translation at the indicated concentrations and incubated for 16 hours at 37° C. (4) RNase A digestion. RNase A (100 µg/ml final concentration) was added at the end of the translation and incubated for 16 hour at 37° C., or added at the end of the 16 hr assembly reaction and incubated for another one hr.

Agarose Gel Electrophoresis and Capillary Transfer.

$^{35}$S-labeled translation reactions were resolved by 1% agarose gel electrophoresis (100 V for ~3 hours), using 6×DNA Loading Buffer Blue (New England Biolabs). The gels were then soaked in 10×SSC (1.5 M NaCl, 150 mM sodium citrate, pH 7.0) for approximately 30 minutes and transferred overnight to nitrocellulose membrane by capillary transfer. The next day the membranes were UV cross-linked and dried in a vacuum oven for 2 hours. The translation products were analyzed by autoradiography and Western blotting with the rabbit polyclonal anti-HBcAg (Dako) or mouse monoclonal anti-woodchuck hepatitis virus core protein (Ning X, et al. (2011) PLoS pathogens 7: e1002255). Cytoplasmic lysates of transfected cells containing HBV capsids were resolved similarly by agarose gel electrophoresis and detected by Western blot analysis as previously described (Ludgate L, et al. (2012). J Virol. 86: 12237-12250; Nguyen D H, Hu J (2008). J Virol 82: 6852-6861).

Sucrose Gradient Fractionation of HBc Capsids Assembled in RRL.

HBc (WT or phosphorylation site mutants) was translated and $^{35}$S-labeled in a 100 µl volume in RRL. In some cases, the translation products were subjected to the indicated enzymatic reactions that had been previously determined to most efficiently induce capsid assembly. The reactions were layered over a 15-30% continuous sucrose gradient (5 ml) and spun in an SW55Ti rotor at 27,000 rpm for 4 hours at 4° C. Two hundred microliter fractions were collected from top to bottom. Individual fractions (10 microL per fraction) along with 0.5 microL translation reaction input were resolved on a 1% agarose gel. The gel was transferred by capillary transfer to nitrocellulose membrane and the capsids detected by autoradiography and Western blotting as described above.

SDS-PAGE and Western Blotting.

$^{35}$S-labeled translation reactions were resolved by SDS-PAGE on 15% or 12.5% polyacrylamide gels. The resolved proteins were transferred to PVDF membrane and detected by autoradiography or Western blotting as above. Cytoplasmic lysates of transfected cells containing HBV capsids were resolved similarly and detected by Western blot analysis as previously described (Ludgate L, et al. (2012). J Virol 86: 12237-12250; Nguyen D H, Hu J (2008). J Virol 82: 6852-6861).

Endogenous Kinase Reaction.

Endogenous kinase reactions were performed as described before (Ludgate L, et al. (2012). J Virol 86: 12237-12250), using 10 µl of (unlabeled) peak sucrose fraction containing the HBV capsids assembled in RRL, in the presence of DMSO (mock treatment) or the indicated kinase inhibitor. The $^{32}$P-labeled capsids or HBc subunits were as a result of the kinase reaction were detected by autoradiography following resolution on an agarose gel or SDS-PAGE, respectively, as described (Ludgate L, et al. (2012). J Virol 86: 12237-12250).

Results

Capsid Assembly from HBc Expressed in RRL Required CTD and could be Modulated by Manipulating the State of CTD Phosphorylation.

It was intriguing that the observation that HBV capsid could assemble efficiently in Xenopus (X.) oocytes when HBc concentrations were less than 1 microM (Seifer M, et al., (1993). J Virol 67: 249-257), which is well below the threshold concentration required for assembly in vitro with purified proteins (ca. 40-80 microM) at physiological salt concentration (Wingfield P T, et al., (1995). Biochemistry 34: 4919-4932; Tan Z, et al. (2013). Journal of Virol 87: 3208-3216). It was decided to test the possibility that HBc translated in RRL may also be able to assemble into capsids even if its concentrations were much lower than those required assembly in vitro. RRL was chosen for in vitro expression due to its ability not only to efficiently translate a variety of proteins but also to facilitate their folding and posttranslational modifications (e.g., see (Ludgate L, et al. (2012). J. Virol 86: 12237-12250; Hu L Seeger C (1996). Proc. Nat'l. Acad. Sci. USA 93: 1060-1064). To allow sufficient time for assembly to occur, HBc was incubated in the translation mix overnight at 37° C., after diluting in a buffer with near physiological salt concentration (see Materials and Methods). The RRL contains protein kinases, including CDK2, that can phosphorylate DHBc at authentic CTD sites as those phosphorylated in vivo (Ludgate L, et al., (2011). PLoS One 6: e29566; Ludgate L, et al. (2012). J Virol 86: 12237-12250), it was considered possible that HBc could be phosphorylated by cellular kinase(s) in the RRL as well. Since CTD phosphorylation state might influence capsid assembly (e.g., by affecting CTD interactions with non-specific RNA), a number of HBc mutants were tested with CTD substitutions that mimic either the nonphosphorylated state (S/T to A) or phosphorylated state (S/T to E) (FIG. 1A) and attempted to manipulate HBc phosphorylation state in RRL by using various inhibitors of cellular kinases or phosphatases. In addition, the HBc truncation mutation (C149) was included with the CTD removed altogether, which is widely used for capsid assembly in bacteria or in vitro.

The concentration of HBc was first estimated when it was translated in the RRL. A quantitative western blot was performed using a serial dilution of recombinant HBV capsids purified from bacteria as standards (FIG. 1B, bottom). As the HBc protein translated in the RRL could be labeled with $^{35}$S-methionine, it could be easily detected also by autoradiography (FIG. 1B, top). It was found that ca. 1 ng HBc was made per microl of translation mix (FIG. 1B) independent of the CTD phosphorylation site substitutions, giving an apparent HBc concentration in RRL ca 50 nM upon translation. The CTD-deleted construct, C149, was expressed at ca. two-fold higher concentration, i.e., 100 nM (FIG. 1B). Thus, the HBc concentrations achieved by translation in RRL were close to but somewhat below the HBc concentrations in the X. oocytes, and far below the threshold required to trigger assembly in vitro. Furthermore, as the translation reactions were diluted ca. 5-fold during the overnight incubation following translation, the HBc concentration during this ("assembly") incubation period was even lower (ca. 10 nM). It was then attempted to detect any capsids that might have formed by resolving the translation mix on an agarose gel, in parallel with a capsid standard purified from bacteria as a migration control (FIG. 2A). A distinct HBc band migrating at the same position on the agarose gel as the capsid standard was detected by both autoradiography (top) and western blot analysis (bottom) in the translation reactions of 3A (lane 3) and 3E mutant HBc (lane 5), in the absence of any additional manipulation. In contrast, the WT HBc migrated much slower as a smear near the top of the gel (lane 1). The CTD-deleted C149 ran also above the capsid band but much faster than the WT HBc (lane 8). As will be described in detail below, the HBc band co-migrating with the capsid standard on the agarose gel was indeed verified to be assembled capsids by sucrose gradient centrifugation; all HBc signals running above this band, including the WT HBc and C149, represented un-assembled subunits.

Given the likelihood of HBc phosphorylation in RRL as mentioned above, the apparent differences in assembly between the WT and the 3A or 3E mutant HBc were intriguing and it was decided to treat the translation mix during the overnight assembly incubation period (i.e., following translation) with an exogenous phosphatase, CIAP, to see if dephosphorylation of the different HBc proteins mediated by CIAP could affect capsid assembly. Remarkably, CIAP treatment induced the assembly of the WT HBc (FIG. 2A, lane 2), but did not have a significant effect on the assembly of the 3A or 3E mutant (FIG. 2A, lanes 4, 6), which assembled even without CIAP treatment as described above. CIAP treatment also did not affect the mobility of the C149 truncation mutant or the unrelated luciferase protein translated in RRL (FIG. 2A, lanes 8-11), evidencing that the effect of CIAP treatment was mediated through the HBc CTD.

Because the buffer components were also modified somewhat in both the mock and CIAP treated reactions shown in FIG. 2A (and repeated in FIG. 2B—lanes 3, 7, 11, 15 for mock incubation and 4, 8, 12, 16 for CIAP incubation), due to the addition of the incubation buffer (see Materials and Methods), which might have affected HBc assembly or migration, the same buffer was added to another set of translation reactions but omitted the overnight incubation (FIG. 2B, lanes 2, 6, 10, 14). In addition, on the same gel another set of samples were run, that didn't have the buffer components nor underwent the overnight incubation (FIG. 2B, lanes 1, 5, 9, 13) to determine if the buffer components alone would affect HBc migration. The same results with the mock and CIAP incubation were obtained in FIG. 2B as in FIG. 2A for the WT, 3A, 3E, and C149 mutants (lanes 3, 4, 7, 8, 11, 12, 15, 16), i.e., 3A and 3E could assemble with or without CIAP, WT assembly required CIAP, and C149 did not assemble even with CIAP. Inclusion of the assembly buffer components alone, without the overnight incubation, was not sufficient to induce assembly of any HBc proteins tested, and the migration of the unassembled HBc proteins was similar with or without the buffer components (lanes 1, 2, 5, 6, 9, 10, 13, 14). Interestingly, the mobility of the WT HBc was affected by the overnight incubation, which caused it to migrate even slower and as a broad smear (FIG. 2B, lane 3 vs. 2). As in FIG. 2A, the mobility of C149 was not affected by any treatment (FIG. 2B, lanes 13-16), indicating again that the effect of overnight incubation or CIAP treatment was mediated through the HBc CTD.

The effects of the 37° C. incubation and the exogenous phosphatase on HBc migration or capsid assembly evidenced that endogenous phosphatase(s) present in RRL might also have influenced HBc migration and capsid assembly. The effects of phosphatase inhibitors were tested on the mobility and capsid assembly by the WT and mutant HBc proteins in RRL, all in the absence of any exogenous phosphatase. Initially, a mixture of non-specific phosphatase inhibitors was used for this purpose. As shown in FIG. 2C, addition of the phosphatase inhibitors during the assembly incubation period completely blocked capsid assembly by 3E (lane 12), decreased slightly assembly by 3A (lane 8), and prevented the mobility change of the WT HBc (lane 4). These results thus confirmed that the RRL indeed contained endogenous cellular phosphatase(s) that could mediate CTD dephosphorylation and consequently was responsible for inducing capsid assembly by mutant HBc 3E, and to a lesser extent, by mutant HBc 3A. In the case of the WT HBc, the putative endogenous phosphatase, in contrast to the exogenous CIAP, was apparently insufficient to induce capsid assembly but could induce the mobility upshift, suggesting that it dephosphorylated the WT HBc as well.

Figure 3:
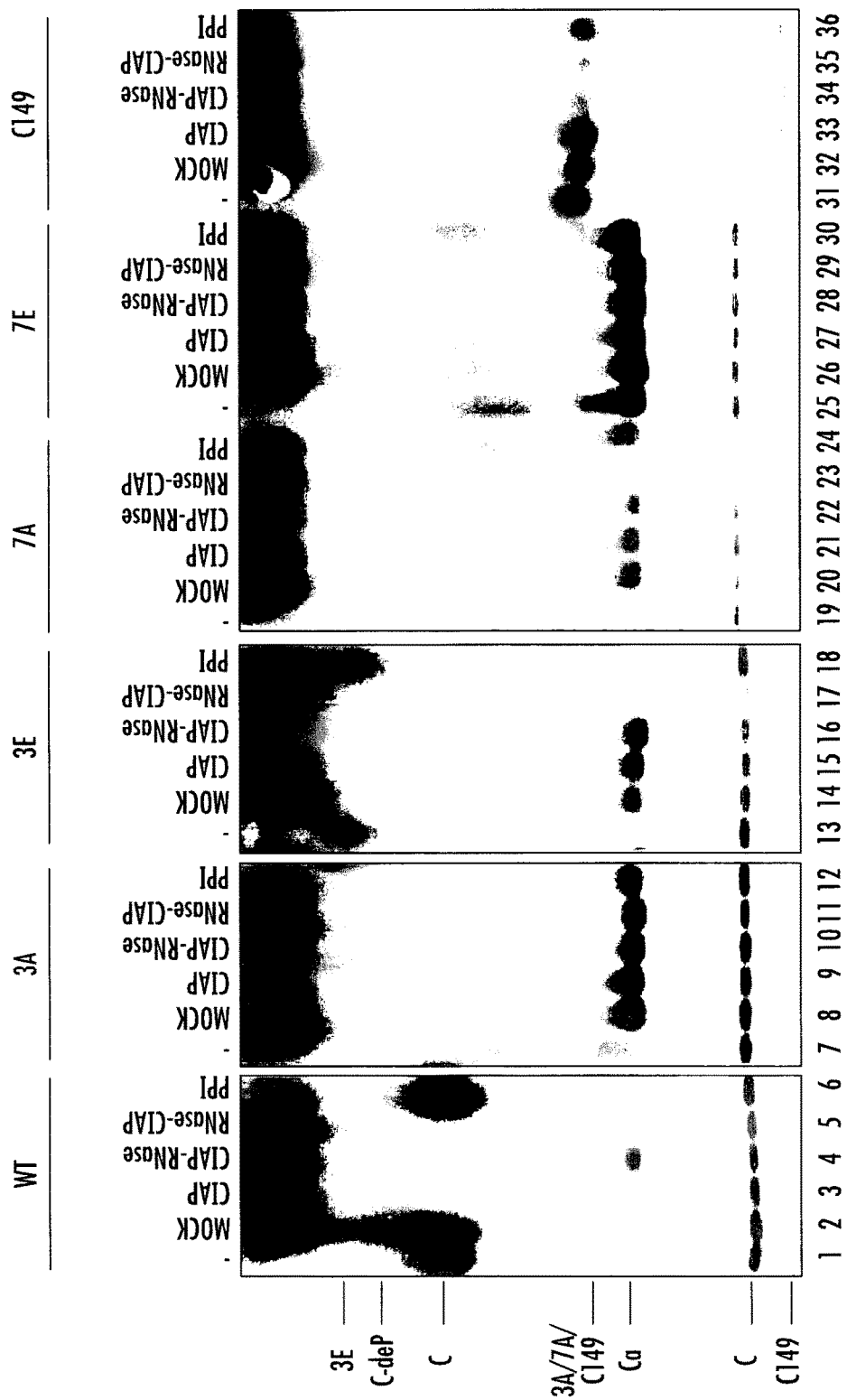
FIG. 3 is a blot showing the effects of exogenous phosphatase, phosphatase inhibitors, and RNase treatment on capsid assembly in RRL. 2 µL RRL translation reaction used, $^{35}$S signals detected by autoradiography. C, full-length HBc protein; Ca, native capsids; C149, C-terminally truncated HBc protein (terminated at position 149); C-deP, dephosphorylated HBc subunits.

To further test the role of CTD phosphorylation state in capsid assembly, two additional CTD phosphorylation mutants 7A and 7E, were included which have all seven confirmed or putative phosphorylation sites in the CTD changed to A and E, respectively. Similar to 3A, 7A was able to assemble into capsids and this assembly was independent of exogenous phosphatase but dependent on the 37° C. incubation (FIG. 3, top, lanes 19-21). Inhibition of the endogenous phosphatase had little effect on 7A assembly (FIG. 3, top, lane 24), consistent with its loss of all CTD phosphorylation sites. Interestingly, the 7E mutant, uniquely among all the HBc proteins tested, appeared to have undergone substantial assembly already by the end of the translation reaction such that most of 7E migrated at the authentic capsid position without the assembly incubation period at 37 C (FIG. 3, top, lane 25). Neither the addition of the exogenous phosphatase or inhibition of the endogenous phosphatase after the translation reaction had any significant effect on its assembly (FIG. 3, top, lanes 26-30).

Whereas the assembled capsids, from either the WT or mutant HBc proteins, all migrated to the same position as the bacterially-derived capsid standard, the mobility of the unassembled HBc proteins was affected by their phosphorylation state. In addition to the upshift of the WT HBc protein induced the endogenous phosphatase as described above, unassembled 3A and 7A, mimicking CTD dephosphorylation, migrated mostly just above the capsid band and comigrating with C149, whereas the phosphomimetic 3E mutant protein migrated mostly on top of the gel above the WT HBc protein but could run as a broad smear from above the assembled capsids to above the unassembled WT HBc (FIGS. 2A-2C and FIG. 3, top) (also see FIG. 4B). The subunit mobility was also to some extent affected by the exact gel and running conditions. There was, however, a general trend that CTD phosphorylation led to retardation of HBc mobility on the agarose gel (3E vs. 3A/7A/C149) but the slight upshift of the WT HBc following dephosphorylation by the putative endogenous phosphatase was opposite to this trend. Assembly of 7E was fast such that little unassembled protein was detected on the agarose gel (FIG. 3, top, lane 25). The exact physical state of the unassembled HBc subunits remains to be characterized but was assumed to be dimers, based on the rapid HBc dimerization observed in the *X. Oocyte* (Zhou S, Standring D (1992). *Proc Natl Acad Sci USA* 89: 10046-10050) and in vitro (Wingfield P T, et al. (1995). *Biochemistry* 34: 4919-4932). As will be described below, the HBc proteins were probably associated with RNA non-specifically in RRL, which would, at least to some extent, account for their mobility on the agarose gel.

The Role of RNA in Capsid Assembly in RRL Depended on CTD Phosphorylation State.

Since the CTD is known to have non-specific RNA binding activity that is modulated by the CTD phosphorylation state, any potential effects of RNA on core protein mobility and more interestingly, on capsid assembly were studied. The translation reactions were treated with RNase before conducting the assembly reaction, or alternatively, treated the reactions with RNase following assembly. With respect to the WT HBc, RNase treatment before CIAP treatment, which was needed to induce WT HBc assembly (FIGS. 2A-2C), prevented capsid assembly (FIG. 3, top, lane 5), thus indicating that RNA indeed played a role in the assembly of the WT capsids. RNase pretreatment also prevented assembly of the 3E mutant (FIG. 3, top, lane 17). On the other hand, it had no effect on assembly of the 3A mutant (FIG. 3, top, lane 11), providing evidence that RNA was not needed or 3A assembly, or alternatively, the 3A mutant was able to protect its bound RNA from RNase digestion as soon as it was translated and before the capsid was fully assembled (see below). In contrast to 3A, 7A assembly was abolished by RNase treatment (FIG. 3, top, lane 23), indicating an essential role for RNA in 7A assembly. On the other hand, RNase treatment had no effect on 7E assembly (FIG. 3, top, lane 29). In contrast to RNase treatment before assembly, RNase treatment following the completion of capsid assembly showed little effect (FIG. 3, top, lanes 4, 10, 16, 22, 28), providing evidence that the assembled capsids were no longer sensitive to RNase and might be able to protect any RNA if it was packaged during assembly (see below).

RNase digestion also affected the mobility of the unassembled core proteins, especially the WT, 3E, and 7A. Indeed, these unassembled proteins became mostly undetectable on the agarose gel (FIG. 3, top, lanes 5, 17, 23), indicating that they either ran off the agarose gel or failed to enter the gel. Even C149, with the CTD entirely removed, was similarly affected by the RNase treatment albeit to a smaller degree (FIG. 3, top, lanes 34, 35). This is consistent with the previous finding that C149 retains some RNA binding activity. The proteins were not simply degraded as a result of the RNase treatment, since the amounts of total core proteins detected by SDS-PAGE were not affected by RNase digestion or any of the manipulations tested (FIG. 3, bottom). As the core proteins are very basic, they presumably failed to migrate toward the anode side (i.e., failed to enter the gel) without bound RNA.

Identification of the Cellular Kinase and Phosphatase in RRL that Modulated CTD Phosphorylation and Capsid Assembly.

The dependence of capsid assembly on CTD and the modulating effects of CTD phosphorylation on assembly in RRL and the mobility of the unassembled HBc proteins provided a convenient cell-free system to identify the cellular kinase(s) and phosphatase(s) responsible for CTD (de)phosphorylation by using specific inhibitors of these enzymes, without the complication of pleiotropic and often toxic effects on manipulating these cellular factors in living cells (Ludgate L, et al. (2012). *J. Virol* 86: 12237-12250). The inventor has recently shown that the cellular CDK2 represents a major host kinase that can phosphorylate the HBc and DHBc CTD, particularly at the three major sites of CTD phosphorylation (all having the SP motif, FIG. 1A). Indeed, it was shown that RRL contained active CDK2 (or at least CDK2-like kinase activity) that can phosphorylate the DHBc CTD (Ludgate L, et al. (2011). *PLoS One* 6: e29566; Ludgate L, et al. (2012). *J. Virol* 86: 12237-12250). The effects of CDK inhibitors were tested on capsid assembly, including a broad spectrum CDK inhibitor (roscovitine) and a specific CDK2 inhibitor. In addition, a broad spectrum inhibitor of PKC was tested since PKC also has been implicated in CTD phosphorylation, and an inhibitor of ERK since ERK (or MAPK) is the other major class of proline-directed kinases, other than CDKs, that are known to phosphorylate the SP motifs.

Figure 4A:
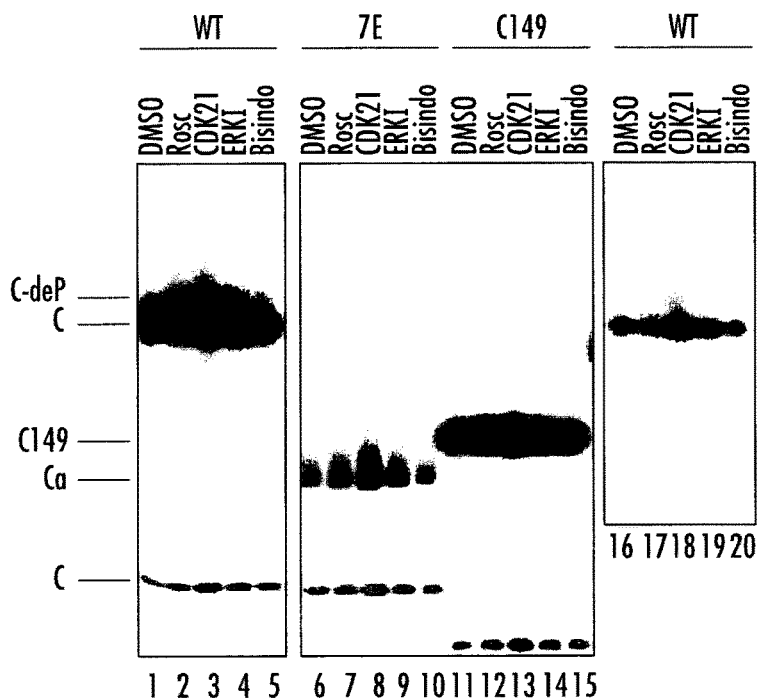
FIGS. 4A, 4B are blots showing the effects of protein kinase inhibitors on capsid assembly in RRL. 1 µL RRL translation reaction used, $^{35}$S signals detected by autoradiography.
Figure 4B:
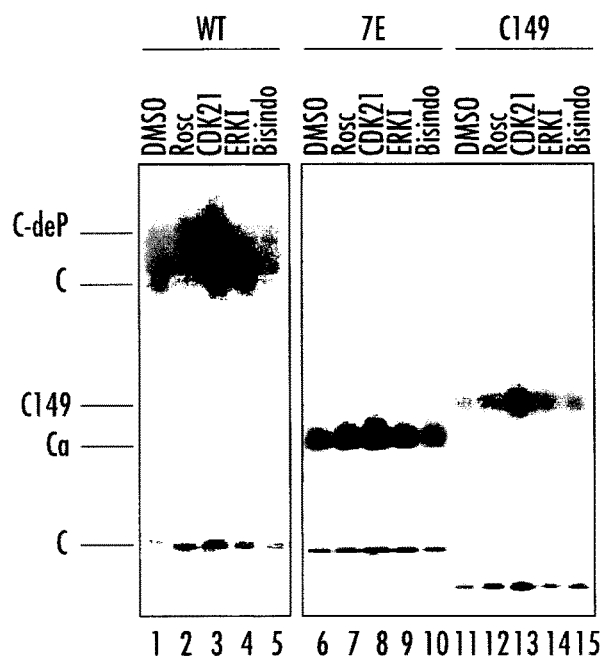

The various inhibitors were added to RRL at the beginning of translation. Upon completion of translation, one aliquot of each translation reaction was loaded without the additional incubation (FIG. 4A) whereas another aliquot underwent the additional overnight incubation at 37 C (FIG. 4B), onto an agarose (top panels) or SDS-polyacrylamide gel (bottom panels). None of the inhibitors tested was able to effect assembly by the WT HBc with or without the overnight incubation (FIG. 4A, top, lanes 1-5, 16-20; 4B, top, lanes 1-5). However, both the broad spectrum CDK inhibitor and the specific CDK2 inhibitor induced a mobility upshift on the agarose gel by a fraction of the WT H8c protein (FIG. 4A, lanes 2, 3, 17, 18; 4B, lanes 2, 3; see also FIGS. 5A-5C for a better separation of dephosphorylated WT HBc from the phosphorylated HBc). As dephosphorylation of the WT HBc by the endogenous RRL phosphatase also caused a similar mobility upshift (by the majority of HBc, in that case) (FIG. 2B, lane 3; FIG. 2C, lanes 2, 3; FIG. 3, top, lane 2; see also FIGS. 5A-5C), this result evidenced that CDK2 was indeed able to phosphorylate the WT HBc in RRL such that inhibition of this kinase produced a similar effect on HBc mobility as its dephosphorylation. As a control, roscovitine and the CDK2 inhibitor had no effect on C149 mobility on the agarose gel (FIGS. 4A and 4B, top, lanes 12, 13), as expected from the deletion of CTD (and thus all it phosphorylation sites) and also consistent with the lack of effect on C149 by the exogenous phosphatase or inhibition of the endogenous phosphatase described above. As another negative control, these two inhibitors also showed little effect on 7E assembly (FIGS. 4A and 4B, top, lanes 7, 8). Although the amounts of capsids assembled in the presence of the CDK2 inhibitor were modestly higher for 7E, the CDK2 inhibitor also appeared to increase, for reasons yet unknown, the levels of the WT and mutant HBc proteins (FIGS. 4A and 4B, bottom) independent of the presence of CTD or substitutions at the CTD. The increased protein levels of these mutants could account for the apparent enhancement of capsid levels in the presence of the CDK2 inhibitor. In contrast to the CDK inhibitors, the PKC and ERK inhibitor showed no effect on either the WT HBc, evidencing that the CTD was not significantly phosphorylated by these kinases in RRL.

Figures 5A, 5B, 5C:
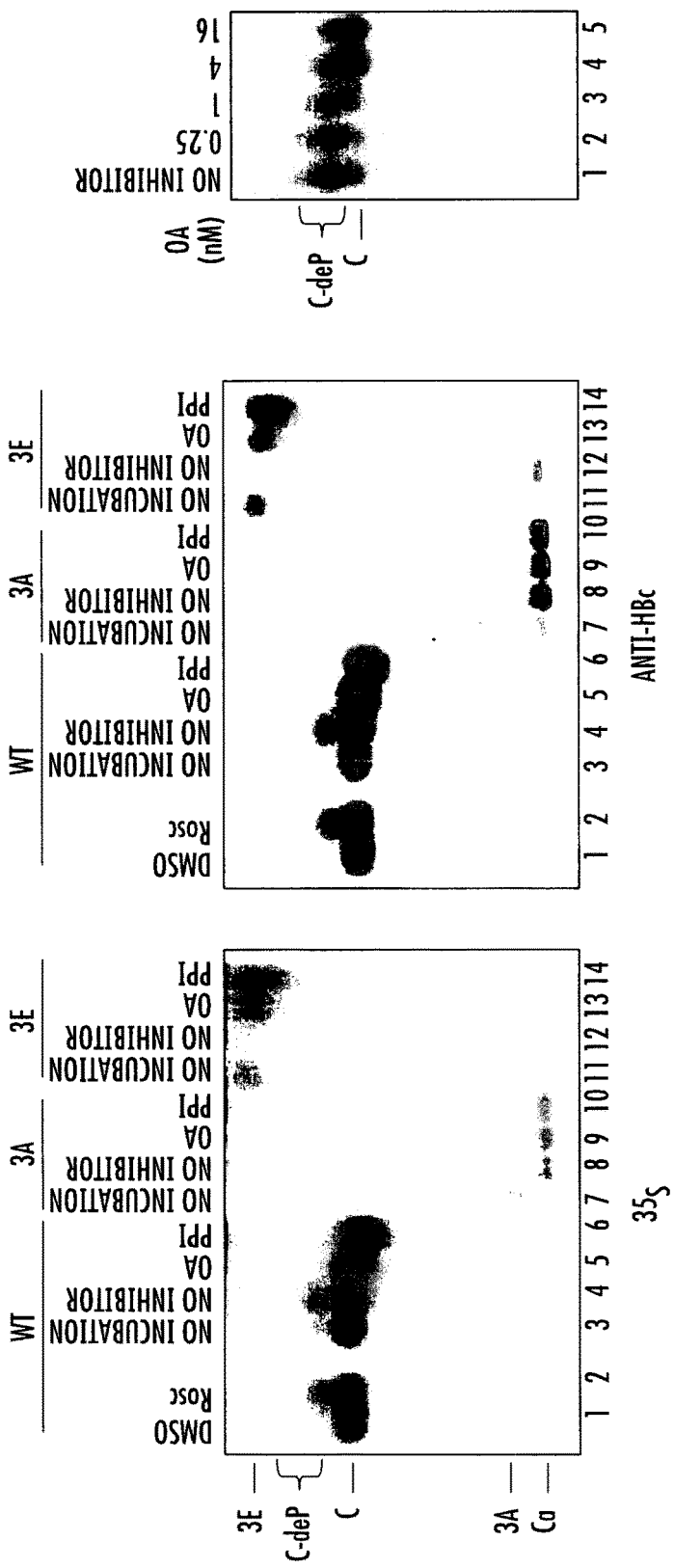
FIGS. 5A-5C are blots showing the effects of different phosphatase inhibitors on capsid assembly in RRL. Each lane contained 2 µl RRL translation reaction.

Regarding the cellular phosphatase(s) that has to mediate CTD dephosphorylation, there is currently no clear candidate(s). The effect of a widely used phosphatase inhibitor, OA, was tested which displays differential activity towards two major cellular serine/threonine phosphatases, PP1 with an $IC_{50}$ of ca. 15-20 nM vs. PP2A with an $IC_{50}$ of ca. 0.1 nM (Cohen P, et al. (1990). *Trends Biochem Sci* 15: 98-102). When added during the overnight 37° C. incubation period following translation, OA (50 nM) completely blocked the mobility upshift of the WT HBc on the agarose gel—as effectively as the mixture of non-specific phosphatase inhibitors (FIGS. 5A and 5B, lanes 5, 6), which would have otherwise been induced by the endogenous RRL phosphatase in the absence of phosphatase inhibition (FIGS. 2A-2C, FIG. 3, FIGS. 4A-4B). The CDK inhibitor roscovitine again induced the mobility upshift as shown in FIGS. 4A and 4B, by inhibiting HBc phosphorylation, which served here as a control for HBc dephosphorylation. In addition, OA also prevented assembly by 3E, similar to the effect of the non-specific phosphatase inhibitor mixture (FIGS. 5A and 5B, lanes 13, 14). In contrast, 3A assembly was not inhibited by OA (or the non-specific phosphatase inhibitor mix) (FIGS. 5A and 5B, lanes 9, 10), consistent with the lack of significant effects of non-specific phosphatase inhibitors on 3A capsid assembly (FIGS. 2A-2C and 3) and probably a lack of significant phosphorylation of 3A in RRL. Titration of OA concentrations showed that 4 nM of OA could significantly affect the dephosphorylation-induced mobility upshift of the WT HBc (FIG. 5C, lane 4), which is far below the $IC_{50}$ for PP1. Although absolute quantification of the lowest OA concentration needed to show an effect on CTD phosphorylation was difficult using the current assay, these results nevertheless suggested that one of the endogenous RRL phosphatase that could mediate CTD dephosphorylation is likely PP2A, but not PP1.

Analysis of Capsid Assembly in RRL by Sucrose Gradient Centrifugation.

To further verify capsid assembly in RRL, the capsids assembled from the WT and mutant HBc proteins translated in RRL were analyzed by sucrose gradient centrifugation, in parallel with a capsid standard purified from bacteria, which was reconstituted into RRL with mock translation to mimic the conditions of capsids assembled in RRL. Based on the results described above, the WT and various HBc mutants were allowed to assemble into capsids under the optimal conditions appropriate for each (FIGS. 6A-6F). Aliquots of unfractionated RRL translation reactions, which didn't undergo any further treatment or treated with CIAP, was loaded in lanes 1 or 2 respectively of FIGS. 6A, 6B, and 6D-6F as controls. As expected, the capsid standard sedimented into the gradient and peaked around fraction 11 (FIG. 6C). C149, which did not show any sign of assembly under any conditions in the preceding figures, also showed no evidence of assembly (FIG. 6F). C149 was incubated with CIAP before sucrose gradient analysis as most other HBc capsids were assembled under the CIAP treatment condition before gradient analysis. The C149 protein stayed on the top of the gradient, and the protein from the top of the gradient migrated fast (just above assembled capsids) on the agarose gel, just as it did in unfractionated RRL (FIG. 6F, lane 1; and FIGS. 2A-2C, FIG. 3, FIGS. 4A-4B).

Figure 6A:
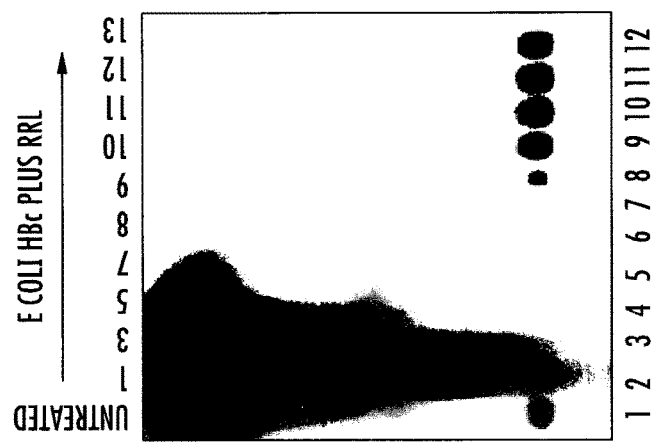
FIGS. 6A-6F are blots showing the analysis of capsid assembly in RRL by sucrose gradient centrifugation. 100 µl reaction separated over linear sucrose gradient. 10 µl per fraction loaded; input RRL translation—ca. 0.5 µl loaded. $^{35}$S signals detected by autoradiography. The peak capsid fraction in each gradient is indicated by the boldface lettering in the labels. Capsids derived from E. coli (unlabeled) in FIG. 6C were detected by western blotting using the anti-HBc antibody. C, full-length HBc protein; Ca, native capsids; C149, C-terminally truncated HBc protein (terminated at position 149).
Figure 6B:
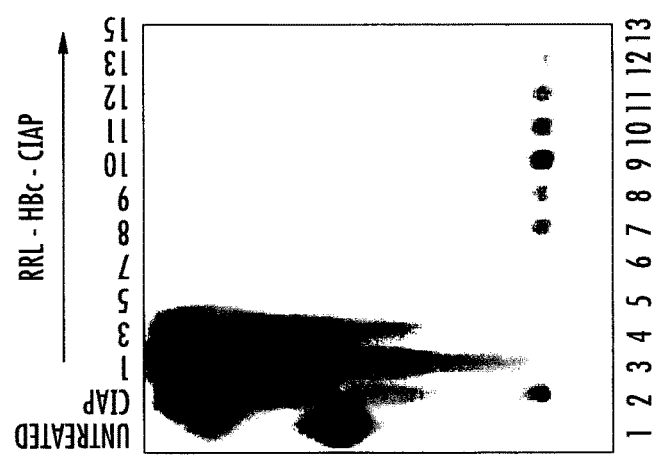
Figure 6C:
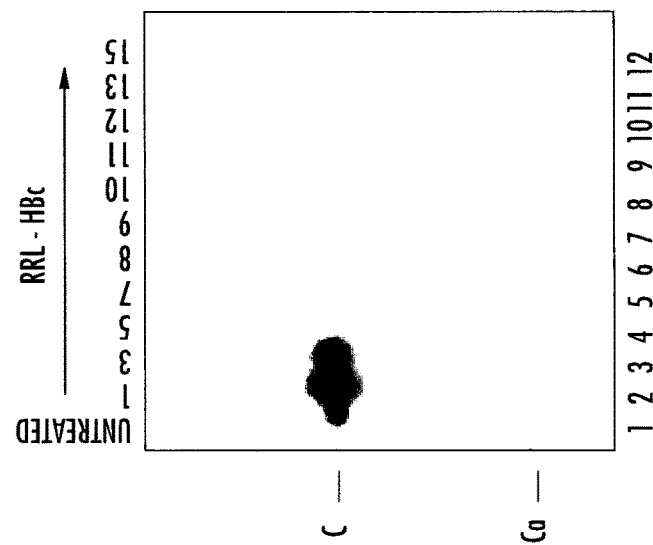
Figure 6F:
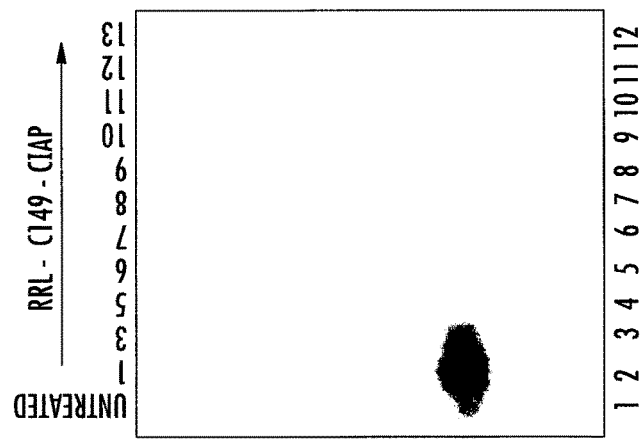
Figure 6E:
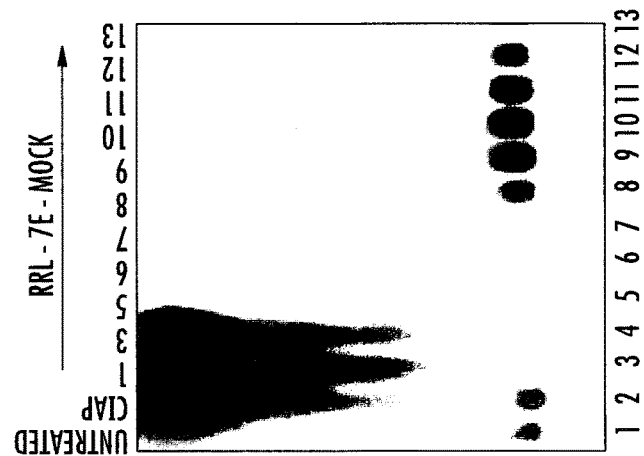
Figure 6D:
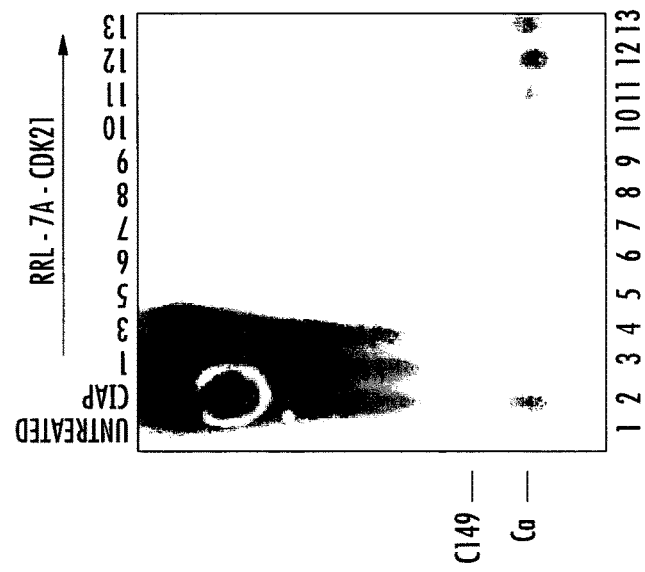

The WT HBc did not assemble into any capsids in the absence of exogenous CIAP and stayed on the top of the gradient (FIG. 6A). The unassembled WT HBc proteins from the top fractions of the gradient also migrated near the top of the agarose gel (FIG. 6A, lanes 2, 3), as shown for the unfractionated translation reactions (FIG. 6A, lane 1; also FIGS. 2A-2C, FIG. 3, FIGS. 4A-4B, FIGS. 5A-5C). In contrast, capsids assembled from CIAP-induced WT HBc sedimented into the middle of the gradient with a peak at fraction 10 (FIG. 6B, lane 9), similar to the capsid standard purified from bacteria. Interestingly, the capsids assembled from 7A sedimented the fastest of all the capsids into the gradient, peaking at fraction 12 (FIG. 6D, lane 12), whereas the 7E capsids sedimented the slowest, peaking at fraction 9 (FIG. 6E, lane 9). The sedimentation of capsids on the sucrose gradient is affected by its interior nucleic acid content, e.g., DS DNA capsids sediments faster than SS or pgRNA capsids. Thus, the difference in sedimentation characteristics on the gradient may provide evidence that the WT and mutant capsids assembled had different structures; in particular, the fairly large difference between 7A and 7E might have reflected the difference in non-specific RNA packaging in the different capsids (see Discussion).

Packaging of CDK2 (or a CDK2-Like Kinase) into Capsids Assembled in RRL.

Figure 7A:
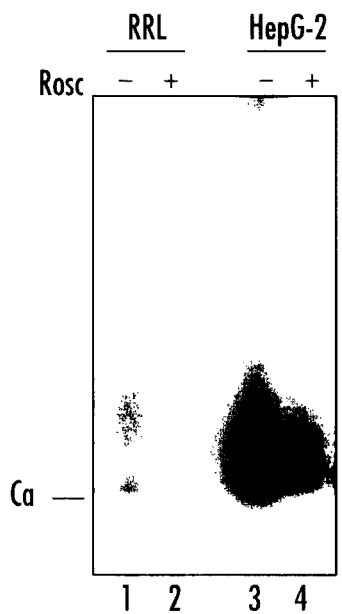
FIGS. 7A, 7B are blots showing the endogenous kinase reaction with capsids assembled in RRL. HBc WT or 3E capsids were assembled in RRL and fractionated by sucrose gradient centrifugation. The peak capsid fractions (10 µl) were used in the endogenous kinase reaction as described in Materials and Methods. WT capsids purified from the human hepatoma cells HepG2 were used as control. Rosc (Roscovitine) was added to 250 µM. Native capsids were resolved by agarose gel electrophoresis (FIG. 7A) or following disruption, the HBc subunits were resolved by SDS-PAGE (FIG. 7B). The $^{32}$P-labeled capsids (FIG. 7A) or HBc subunits (FIG. 7B), as a result of the endogenous kinase reaction, were detected by autoradiography. C: full-length HBc protein; Ca, native capsids.
Figure 7B:
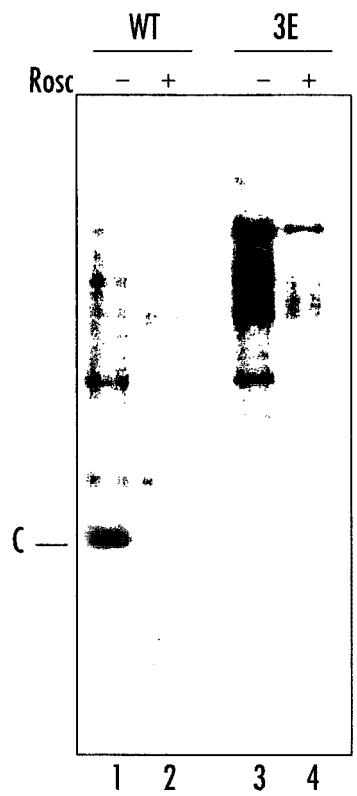

HBV capsids assembled in the human liver, hepatoma cells in culture, or even insect cells package a host-derived protein kinase that can use the capsid protein as a substrate (i.e., the endogenous kinase). Kinase packaging is independent of any other viral proteins. CDK2 (or at least, a kinase closely related to CDK2 biochemically and immunologically) represents a major endogenous kinase. It was thus determined, whether the capsids assembled in RRL also packaged a kinase from RRL, especially since it was found that CDK2 was likely involved in phosphorylating the CTD in RRL (FIGS. 4A-4B). Indeed, an endogenous kinase assay revealed that capsids assembled from the WT HBc packaged a kinase that could phosphorylate the capsid protein and was sensitive to inhibition by the CDK inhibitor roscovitine (FIGS. 7A and 7B, lanes 1, 2), similar to the capsids purified from HepG2 cells assayed in parallel (FIG. 7A, lanes 3, 4). The capsids assembled from 3E did not show such an endogenous kinase reaction (FIG. 7B, lanes 3, 4), evidencing that it failed to package a kinase. Alternatively, the 3E capsids might have packaged a kinase but the sites phosphorylated by such a kinase were lost in the 3E mutant. Regardless, these results evidenced that capsids assembled in RRL did indeed package CDK2 (or CDK2-like) kinase, similar to those assembled in mammalian or insect cells.

Analysis of Non-Specific RNA Packaging by Capsids Assembled in Mammalian and Bacterial Cells.

Figures 8A, 8B, 8C:
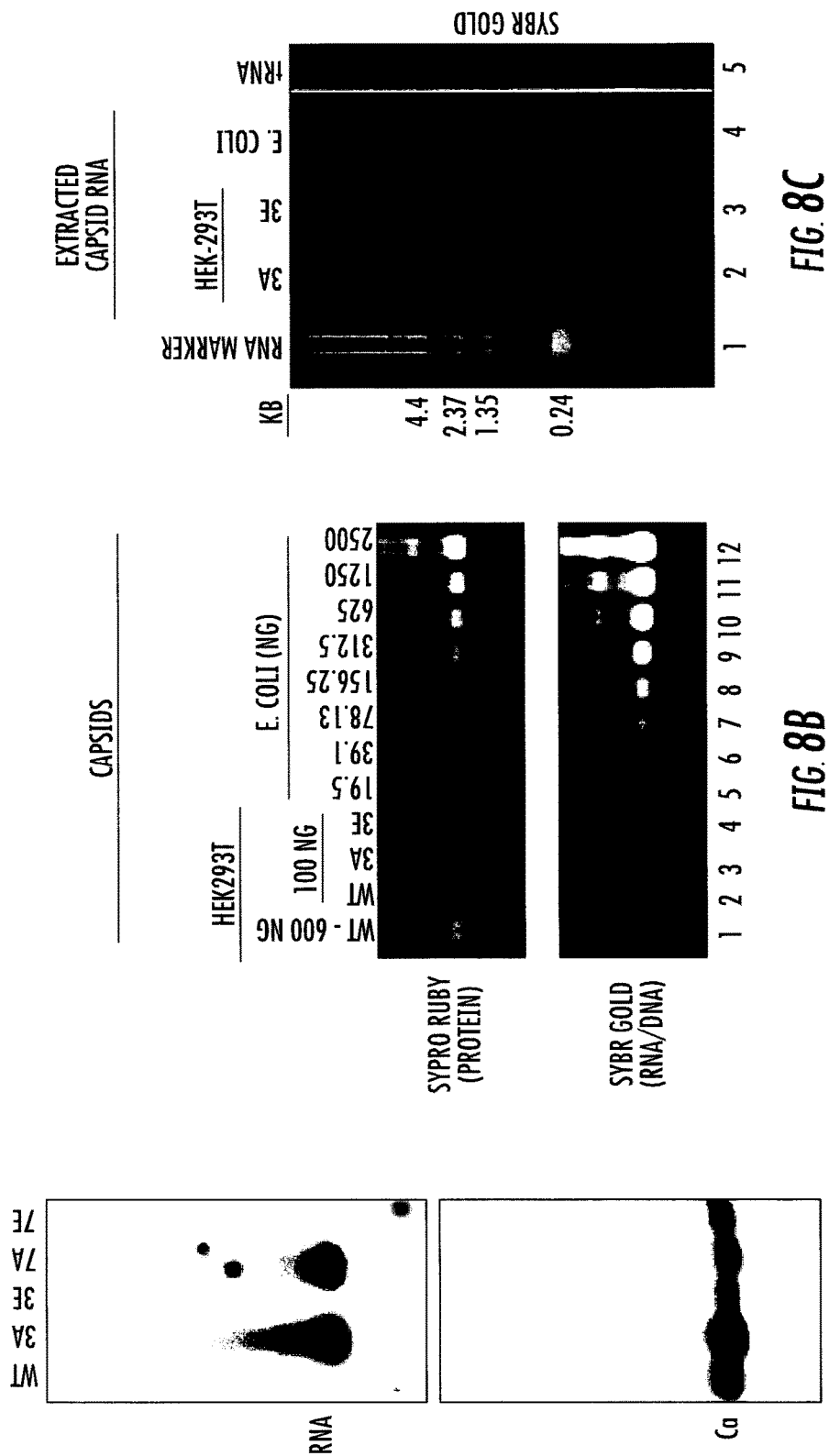
FIGS. 8A-8C show the analysis of non-specific RNA packaging by capsids assembled in mammalian and bacterial cells. The indicated WT and mutant HBc expression constructs were transfected into HepG2 (FIG. 8A) or HEK289T (FIGS. 8B, 8C) cells. Cytoplasmic lysate from transfected HEK293T cells were resolved on an agarose gel and transferred to nitrocellulose membrane. Packaged HBc mRNA was detected by $^{32}$P-labeled anti-sense HBV riboprobe (FIG. 8A, top) and the capsid (Ca) by anti-HBc antibody (FIG. 8A, bottom). Capsids purified by sucrose gradient centrifugation from transfected HEK293T cells (FIG. 8B, lanes 1-4.

In FIGS. 8A-8C, the indicated WT and mutant HBc expression constructs were transfected into HepG2 (FIG. 8A) or HEK289T (FIGS. 8B, 8C) cells. Cytoplasmic lysate from transfected HEK293T was resolved on an agarose gel and transferred to nitrocellulose membrane. Packaged HBc mRNA was detected by $^{32}$P-labeled anti-sense HBV riboprobe (FIG. 8A, top) and the capsid (Ca) by anti-HBc antibody (FIG. 8A, bottom). Capsids purified by sucrose gradient centrifugation from transfected HEK293T cells (FIG. 8B, lanes 1-5; FIG. 8C, lanes 2, 3) or E. coli (FIG. 8B, lanes 6-12; FIG. 8C, lane 4) were resolved on an agarose gel and detected by Spyro Ruby staining (FIG. 8B, top) and their associated nucleic acid by Sybr Gold staining (FIG. 8B, bottom). In addition, nucleic acid from the purified capsids was isolated and resolved on an agarose gel and detected by Sybr Gold staining (FIG. 8C). The RNA marker and tRNA were also loaded as size standards (FIG. 8C, lanes 1 and 5, respectively).

The results obtained showed that HBc WT failed to package non-specific RNA when expressed in mammalian cells, in contrast to the same capsids assembled in E. coli. Preventing HBc phosphorylation in the 3A and 7A mutants led to packaging of both the HBc mRNA as well as small cellular RNAs (likely tRNA). The amount of RNA packaging by the 3A mutant in mammalian cells was similar to that packaged by the WT capsids in E. coli. In contrast, the phosphomimetic 3E and 7E mutants failed to package, or packaged much less, RNA.

Analysis of HBc expression and capsid assembly in mammalian cells. In FIGS. 9A and 9B, the indicated WT and mutant HBc expression constructs were transfected into HepG2 (FIG. 9A, lanes 1-4) or HEK289T (FIG. 9A, lanes 5-8; FIG. 9B, lanes 1-3) cells. Cytoplasmic lysate from transfected cells was resolved on an agarose gel and transferred to nitrocellulose membrane, and capsids (Ca) were detected by anti-HBc antibody (FIGS. 9A and 9B, top). The lysate was also resolved by SDS-PAGE and the core subunits (C—full length or WT, C149, C149R) detected by western blotting using anti-HBc antibody (FIG. 9A, middle and bottom; FIG. 9B, bottom).

The results obtained showed that C149, without the CTD failed to accumulate in mammalian cells, most likely due to its failure to assemble into stable capsids and consequent degradation as subunits. Appending 4 arginine residues to C149 could rescue capsid expression and assembly, most likely by restoring non-specific RNA binding activity that nucleated capsid assembly.

DISCUSSION

Low HBc concentration condition in RRL, as in host cells, CTD needed for assembly, which was further modulated by CTD state of phosphorylation. Non-specific RNA binding by CTD plays a role in assembly in RRL but CTD could also facilitate assembly even in the absence of RNA binding or packaging. Packaging of CDK2 (or a CDK2-like kinase) during assembly in RRL as in cells.

Potential host factors involved in assembly: wheat germ extract assembly with translation of full-length HBc—the cytosolic chaperonin TRiC complex was implicated as a host factor that facilitates capsid assembly (Lingappa J R, et al. (1994). *J Cell Biol* 125: 99-111); in vitro, SRPK as a putative chaperone binding to CTD (Chen C, et al. (2011). *PLoS Pathog* 7: e1002388). However, the in vitro assembly reaction of empty capsids, with or without SRPK, requires high HBc concentration (ca. 5-15 microM) and high salt concentration (250 mM) (Porterfield J Z, et al. (2010). *J Virol* 84: 7174-7184; Chen C, et al. (2011). *PLoS Pathog* 7: e1002388), neither of which is physiological. The RRL system reported here represents a more physiologically relevant system that allows the study of HBV capsid assembly under cell-free conditions that more closely mimic in vivo cellular environment. In particular, the role of CTD and its state of phosphorylation, and N-terminal acetylation state of HBc on assembly can be dissected. The role of specific host factors in modulating capsids assembly, by mediating HBc modifications or via other mechanisms, can also be studied in detail. Already obtained is the evidence presented here for CDK, PPase (PP2A). Moreover, a step forward was taken to constructing authentic, replication-competent nucleocapsids containing the RT-pgRNA complex under cell-free conditions. Also antiviral development targeted at capsid assembly was facilitated. Prior to these studies presented herein, only NTD has been targeted (Deres K, et al. (2003). *Science,* 299: 893-896; Stray S L, et al. (2005). *Proc. Nat'l Acad. Sci.* USA 102: 8138-8143), whereas the results presented herein evidence that CTD may also be viable target, both CTD itself and host factors that modulate CTD modification and functions.

What is claimed is:

1. A method for assembling Hepatitis virus capsids in vitro comprising: transcribing, translating or expressing one or more hepatitis virus capsid or core protein nucleic acids, polynucleotides, oligonucleotides, proteins, peptides, mutants or fragments thereof, which encodes for or comprises a hepatitis virus capsid or core protein C-terminal Domain (CTD) and N-terminal domain (NTD) sufficient to form capsids, in a rabbit reticulocyte lysate (RRL) cell-free system, said RRL cell-free system comprising at least one host factor for controlling a phosphorylation state of a capsid protein, said at least one host factor being Cyclin-dependent kinase 2 (CDK2) or Protein phosphatase 2 (PP2A).

2. The method of claim 1, wherein an assembled Hepatitis virus capsid comprises one or more agents encapsulated therein.

3. The method of claim 2, wherein the one or more agents comprise: chemotherapeutic agents, anti-virus agents, antiinflammatory agents, nucleic acids, vectors, expression vectors, polynucleotides, oligonucleotides, proteins, peptides, lipids, lipoproteins, organic molecules, inorganic molecules, synthetic compounds, natural compounds, saccharides, or combinations thereof.

4. The method of claim 1, wherein the assembled hepatitis virus capsid is a non-replicating and/or non-infecting hepatitis B virus capsid.

* * * * *

```
SEQUENCE LISTING

<160> NUMBER OF SEQ ID NOS: 2

<210> SEQ ID NO 1
<211> LENGTH: 34
<212> TYPE: PRT
<213> ORGANISM: Hepatitis B virus

<400> SEQUENCE: 1

Arg Arg Arg Gly Arg Ser Pro Arg Arg Thr Pro Ser Pro Arg Arg
1               5                  10                  15

Arg Arg Ser Gln Ser Pro Arg Arg Arg Ser Gln Ser Arg Glu Pro
            20                  25                  30

Gln Cys

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Arg
1
```